United States Patent
Goussev et al.

(10) Patent No.: US 11,305,268 B2
(45) Date of Patent: Apr. 19, 2022

(54) HYDROGENATION AND DEHYDROGENATION CATALYST, AND METHODS OF MAKING AND USING THE SAME

(71) Applicants: Dmitri Goussev, Waterloo (CA); Denis Spasyuk, Saskatoon (CA)

(72) Inventors: Dmitri Goussev, Waterloo (CA); Denis Spasyuk, Saskatoon (CA)

(*) Notice: Subject to any disclaimer, the term of this patent is extended or adjusted under 35 U.S.C. 154(b) by 0 days.

(21) Appl. No.: 16/740,764

(22) Filed: Jan. 13, 2020

(65) Prior Publication Data
US 2020/0147597 A1 May 14, 2020

Related U.S. Application Data

(62) Division of application No. 14/239,179, filed as application No. PCT/CA2012/050571 on Aug. 20, 2012, now Pat. No. 10,583,427.

(60) Provisional application No. 61/593,840, filed on Feb. 1, 2012, provisional application No. 61/524,815, filed on Aug. 18, 2011.

(51) Int. Cl.
| | | |
|---|---|---|
| *B01J 31/00* | (2006.01) | |
| *B01J 31/24* | (2006.01) | |
| *C07F 15/00* | (2006.01) | |
| *C07F 9/58* | (2006.01) | |
| *C07B 31/00* | (2006.01) | |
| *B01J 31/20* | (2006.01) | |
| *B01J 31/22* | (2006.01) | |
| *C01B 3/02* | (2006.01) | |
| *C07C 29/149* | (2006.01) | |
| *C07C 41/18* | (2006.01) | |
| *C07C 209/70* | (2006.01) | |
| *B01J 31/18* | (2006.01) | |

(52) U.S. Cl.
CPC .......... *B01J 31/2471* (2013.01); *B01J 31/20* (2013.01); *B01J 31/2295* (2013.01); *B01J 31/2404* (2013.01); *B01J 31/2461* (2013.01); *C01B 3/02* (2013.01); *C07B 31/00* (2013.01); *C07C 29/149* (2013.01); *C07C 41/18* (2013.01); *C07C 209/70* (2013.01); *C07F 9/58* (2013.01); *C07F 15/002* (2013.01); *C07F 15/0046* (2013.01); *C07F 15/0053* (2013.01); *B01J 31/189* (2013.01); *B01J 2231/763* (2013.01); *B01J 2531/0205* (2013.01); *B01J 2531/0238* (2013.01); *B01J 2531/821* (2013.01); *B01J 2531/825* (2013.01); *Y02E 60/36* (2013.01)

(58) Field of Classification Search
None
See application file for complete search history.

(56) References Cited

FOREIGN PATENT DOCUMENTS

| JP | 2019-242304 A | 10/2009 |
| WO | 2007/013931 A2 | 2/2007 |

OTHER PUBLICATIONS

Zotto et al. (Organometallics, 26, 2007, 5636-5642 (Year: 2007).*
Morris et al. (Inorganic Chemistry, 49, 2010, 1094-1102 (Year: 2010).*
Konrad, "New PNHN Pincer-Type Ligands and Their Complexes for Transfer Hydrogenation", A thesis presented to the University of Waterloo in fulfillment of the thesis requirement for the degree of Master of Science in Chemistry, 2009; 88 pages.
Ekambaram Balaraman et al.; "Efficient hydrogenation of organic carbonates, carbamates and formates indicates alternative routes to methanol based on CO2 and CO"; nature chemistry; ARTICLES; pp. 609-614 published online: Jul. 22, 2011; DOI.10.1038/NCHEM.1089.
Michael J. Sgro et al.; "Ni(II), Pd(I) and Pt(II) complexes of PNP and PSP tridentate amino-phosphine ligands" Dalton Transactions; vol. 41; 2012; pp. 6791-6802.
Reena Singh et al.; "Iron(III) complexes using NNS reduced Schiff bases and NNOS coordinating tetradentate igands: Synthesis, structure and catecholase activity"; Inorganica Chimica Acta; vol. 363; Issue 12; Oct. 15, 2010 pp. 3131-3138; doi.org/10.1016/j.ica.2010.05.027.
Japanese Office Action dated Apr. 5, 2016, in connection with corresponding JP Application No. 2014-525271 (8 pgs., English translation only being provided).
Deborah C. Bebout, et al., "Bis-tridentate chelates of an asymmetric lignad: X-ray structures and solution NMR characterization of divalent zinc triad metal ion complexes of N-(2-pyridylmethyl)-N-(2-(methylthio)ethyl)amine", in Polyhedron, vol. 27, 2008, pp. 1591-1600 (10 pgs.).
Yasuhiro Funahashi, et al., "Complex Formation and Redox Reactions in Copper-Pterin Cofactor Systems, Possible Relevance to Phenylalanine Hydroxylase", in Bulletin of the Chemical Society of Japan, vol. 72, No. 3, 1999, pp. 415-424 (11 pgs.).

(Continued)

*Primary Examiner* — Yun Qian
(74) *Attorney, Agent, or Firm* — Maier & Maier, PLLC

(57) ABSTRACT

The present application discloses complexes useful as catalysts for organic chemical synthesis including hydrogenation and dehydrogenation of unsaturated compounds or dehydrogenation of substrates. The range of hydrogenation substrate compounds includes esters, lactones, oils and fats, resulting in alcohols, diols, and triols as reaction products. The catalysts of current application can be used to catalyze a hydrogenation reaction under solvent free conditions. The present catalysts also allow the hydrogenation to proceed without added base, and it can be used in place of the conventional reduction methods employing hydrides of the main-group elements. Furthermore, the catalysts of the present application can catalyze a dehydrogenation reaction under homogenous and/or acceptorless conditions. As such, the catalysts provided herein can be useful in substantially reducing cost and improving the environmental profile of manufacturing processes for variety of chemicals.

9 Claims, 3 Drawing Sheets

(56) References Cited

OTHER PUBLICATIONS

Paraskevi O. Lagaditis, et al., "Template Synthesis of Iron(II) Complexes Containing Tridentate P-N-S, P-N-P, P-N-N, and Tetradentate P-N-N-P Ligands", in Inorganic Chemistry, vol. 49, 2010, pp. 1094-1102 (9 pgs.).

Elisa Palma, et al., "A pyrazolylamine-phosphonate monoester chelator for the fac-[M(CO)3]+ core (M=Re, 99mTc) Synthesis, coordination properties and biological assessment", in the Journal of Labeled Compounds and Radiopharmaceuticals (JLCR), vol. 50, 2007, pp. 1176-1184 (9 pgs.).

Dalili, S et al., "Aziridine-derived iminophosphine ligands in palladium-catalyzed allylic substitution," Journal of Organometallic Chemistry, 2004, 3604-3611, 689, Science Direct, Ontario, Canada.

Milstein, D, "Discovery of Environmentally Benign Catalytic Reactions of Alcohols Catalyzed by Pyridine-Based Pincer Ru Complexes BAsed on Metal-Ligand Cooperation," Topics in Catalysis, 2010, 915-923, 53, Springer Science +Business Media, LLC, Rehovot, Israel.

St Au Bitz, A et al., "Catalytic Dehydrocoupling/Dehydrogenation of N-Methylamine-Borane andAmmonia-Borane Syntheses and Characterization of High Molecular Weight Polyaminoboranes," Journal of the American Chemical Society, 2012, 13332-13345, 132, JACS ARticles, Munich, Germany.

PCT/CA2012/050571 International Search Report dated Nov. 9, 2012.

PCT/CA2012/050571 Written Opinion of the International Searching Authority dated Nov. 9, 2012.

PCT/CA2012/050571 Written Opinion of the International Preliminary Examining Authority dated Dec. 4, 2013.

PCT/CA2012/050571 International Preliminary Report on Patentability dated Jan. 2, 2014.

Extended European Search Report dated Mar. 3, 2015, including the Supplementary European Search Report and the European Search Opinion, in EP Application No. 12824170.0-1451/2744815 (PCT/CA2012/050571).

D. Spasyuk, et al., "From Esters to Alcohols and Back with Ruthenium and Osmium Catalyst", in Angewandte Chemie International Edition, vol. 51, No. 11, Mar. 12, 2012, pp. 2772-2775 (Document 1).

D. Spasyuk, et al., "Acceptorless Dehydrogenative Coupling of Ethanol and Hydrogenation of Esters and Imines", in Organometallics, vol. 31, No. 15, Aug. 13, 2012, pp. 5239-5242. (Document 2).

M. Fujita, et al., "Metal-Chelating Inhibitors of a Zinc Finger Protein HIV-EP1, Remarkable Potentiation of Inhibitory Activity by Introduction of SH Groups", in the Journal of Medicinal Chemistry, Jan. 1, 1996, pp. 503-507. (Document 3).

Chinese Office Action dated Jun. 18, 2015, in connection with corresponding CN Application No. 201280043959.2 (15 pgs.).

T. Morimoto, et al., "Enantioselective copper-catalyzed conjugate addition of diethylzinc to enones using new chiral P, N ligands composed of (S)-2-alkyl-2-aminoethylphosphines and α-substituted pyridines", in Tetrahedron Letters, vol. 11, Dec. 31, 2000, pp. 10025-10029. (Document 1).

* cited by examiner

HYDROGENATION AND DEHYDROGENATION CATALYST, AND METHODS OF MAKING AND USING THE SAME

CROSS-REFERENCE TO RELATED APPLICATIONS

This is a Divisional application of a non-provisional application having U.S. patent application Ser. No. 14/239,179 filed on May 27, 2014, the National Phase application of International Application No. PCT/CA2012/050571 filed on Aug. 20, 2012, U.S. Provisional Application No. 61/524,815 filed on Aug. 18, 2011, and U.S. Provisional Application No. 61/593,840 filed on Feb. 1, 2012, the contents of which are all incorporated herein by reference.

FIELD OF THE INVENTION

The present invention pertains to catalysts. More specifically, the present invention pertains to catalysts useful in hydrogenation and dehydrogenation reactions.

INTRODUCTION

Reduction of esters is one of the most fundamental organic reactions and is useful for synthesis of a variety of useful organic alcohols. The reduction of esters is typically accomplished using main-group hydride reagents, such as LiAlH$_4$, or using molecular hydrogen. The use of hydride reducing reagents is inconvenient and expensive, particularly on a large scale; furthermore, this approach generates large amounts of chemical waste. The hydride reduction method can also be dangerously exothermic at the stage of quenching and it can be difficult to control. The catalytic reduction of esters under hydrogen gas is, in all respects, a very attractive 'green' alternative to the classical hydride reduction.

A key aspect of the ester reduction with molecular hydrogen is the catalytic system utilized in the process that can rapidly bind and split molecular hydrogen to give a transition-metal hydride. The development of highly efficient and useful catalysts and catalytic systems for hydrogenation of lactones, esters, oils, and fats is an important need in chemistry. Particularly, developing hydrogenation processes operating in the temperature range of 20 to 100° C. using less than 1000 ppm (0.1 mol %) catalyst under relatively low H$_2$ pressure (1-50 bar) is highly desirable. Among the few catalysts and catalytic systems capable of converting esters and lactones into alcohols and diols under hydrogen gas, the presently most useful and efficient are complexes of transition metals, such as ruthenium, with bidentate phosphine-amine or tetradentate phosphine-imine ligands as described in Publication No. US 2010/0280273 A1 and in *Angew. Chem. Int. Ed.* 2007, 46, 7473, incorporated herein by reference. Typical ruthenium catalyst loadings of 500-1000 ppm (0.05-0.1 mol %) are used, however, the major drawback of such methods is the need for a large amounts of base (5-10 mol %) such as NaOMe, thereby reducing the product selectivity and generating large amounts of chemical waste due to the need for product neutralization and extensive purification. Furthermore, no hydrogenation of naturally occurring esters, e.g. plant oils such as olive oil, to give unsaturated fatty alcohols was reported with the ruthenium catalysts. Fatty alcohols behave as nonionic surfactants due to their amphiphilic nature. They find use as emulsifiers, emollients and thickeners in the cosmetics and food industries, and as industrial solvents. Fatty alcohols are also very useful in the production of detergents and surfactants, and they have a potential in the production of biodiesel.

The development of green chemical processes and the use of biomass for hydrogen production have attracted much attention in recent years. Significant progress in dehydrogenation of bio-alcohols (chiefly ethanol) has been achieved with heterogeneous catalysts, however, at the cost of using drastic reaction conditions, such as high temperature (>200° C.) and pressure. Therefore, designing well-defined homogeneous catalysts for the dehydrogenation of alcohols under mild conditions represents an important scientific and practical goal.

There has been little progress in the area of acceptorless dehydrogenation of primary alcohols since Cole-Hamilton and co-workers demonstrated dehydrogenation of ethanol catalyzed by [RuH$_2$(N$_2$)(PPh$_3$)$_3$], where an excess of NaOH, high temperature (150° C.), and an intense light source were needed to achieve TOF=210 h$^{-1}$, after 2 h (D. Morton, D. J. Cole-Hamilton, I. D. Utuk, M. Paneque-Sosa, M. Lopez-Poveda, *J. Chem. Soc. Dalton Trans.* 1989, 489; D. Morton, D. Cole-Hamilton, *J. Chem. Soc. Chem. Commun.* 1988, 1154; and D. Morton, D. J. Cole-Hamilton, *J. Chem. Soc. Chem. Commun.* 1987, 248). In recent years, several new homogeneous catalysts for acceptorless dehydrogenative coupling of primary alcohols have been developed and studied, such as the systems published by Milstein and co-workers (for a review see: D. Milstein, *Top. Catal.* 2010, 53, 915). However, all these new catalysts are inactive at temperatures below 100° C., for example, for converting ethanol and propanol to hydrogen and ethyl acetate and propyl propionate, respectively.

Therefore, there remains a need for efficient metal catalysts for the hydrogenation of esters, lactones, and fats and oils derived from natural sources, which could operate under base-free conditions and using relatively low reaction temperature and hydrogen pressure. There also remains a need for catalysts capable of efficient alcohol dehydrogenation under mild, and preferably neutral, reaction conditions, for environmentally benign production of esters and lactones from alcohols and diols, respectively, accompanied by formation of hydrogen gas.

The above information is provided for the purpose of making known information believed by the applicant to be of possible relevance to the present invention. No admission is necessarily intended, nor should be construed, that any of the preceding information constitutes prior art against the present invention.

BRIEF DESCRIPTION OF THE FIGURES

For a better understanding of the present invention, as well as other aspects and further features thereof, reference is made to the following description which is to be used in conjunction with the accompanying drawings, where.

DESCRIPTION OF THE INVENTION

Figure 1:
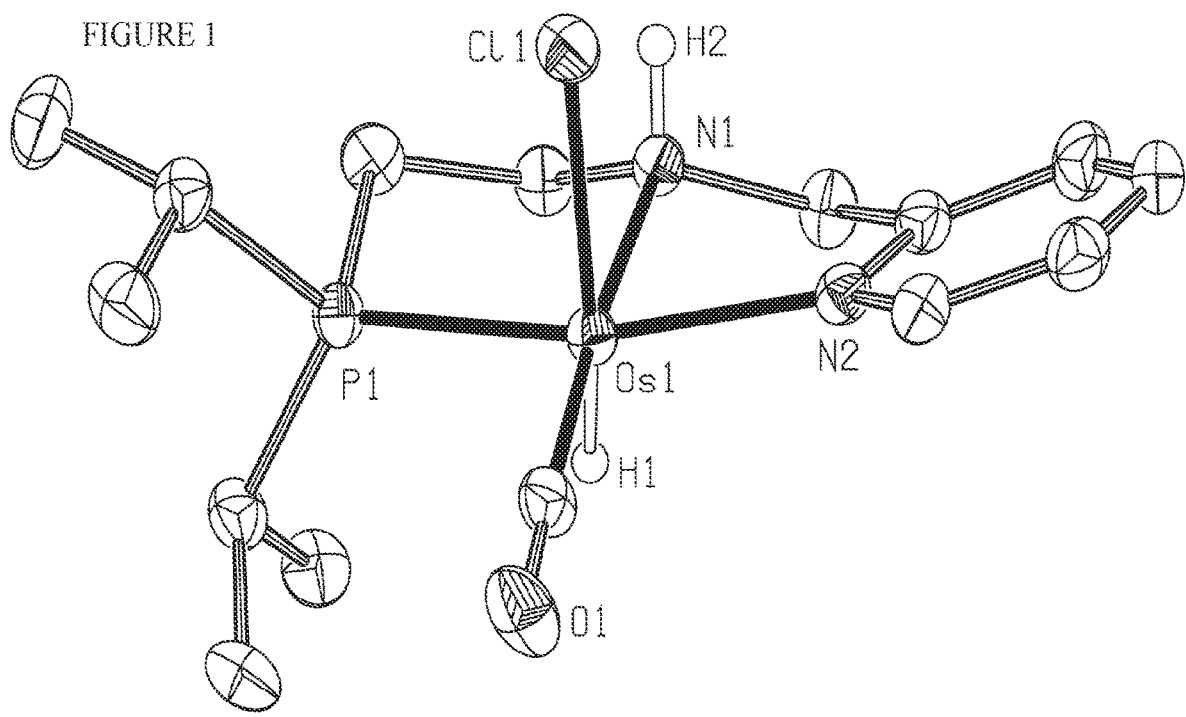
FIG. 1 is an ORTEP diagram for complex 1, thermal ellipsoids are at 50% probability (the hydrogen atoms are omitted for clarity)
Figure 2:
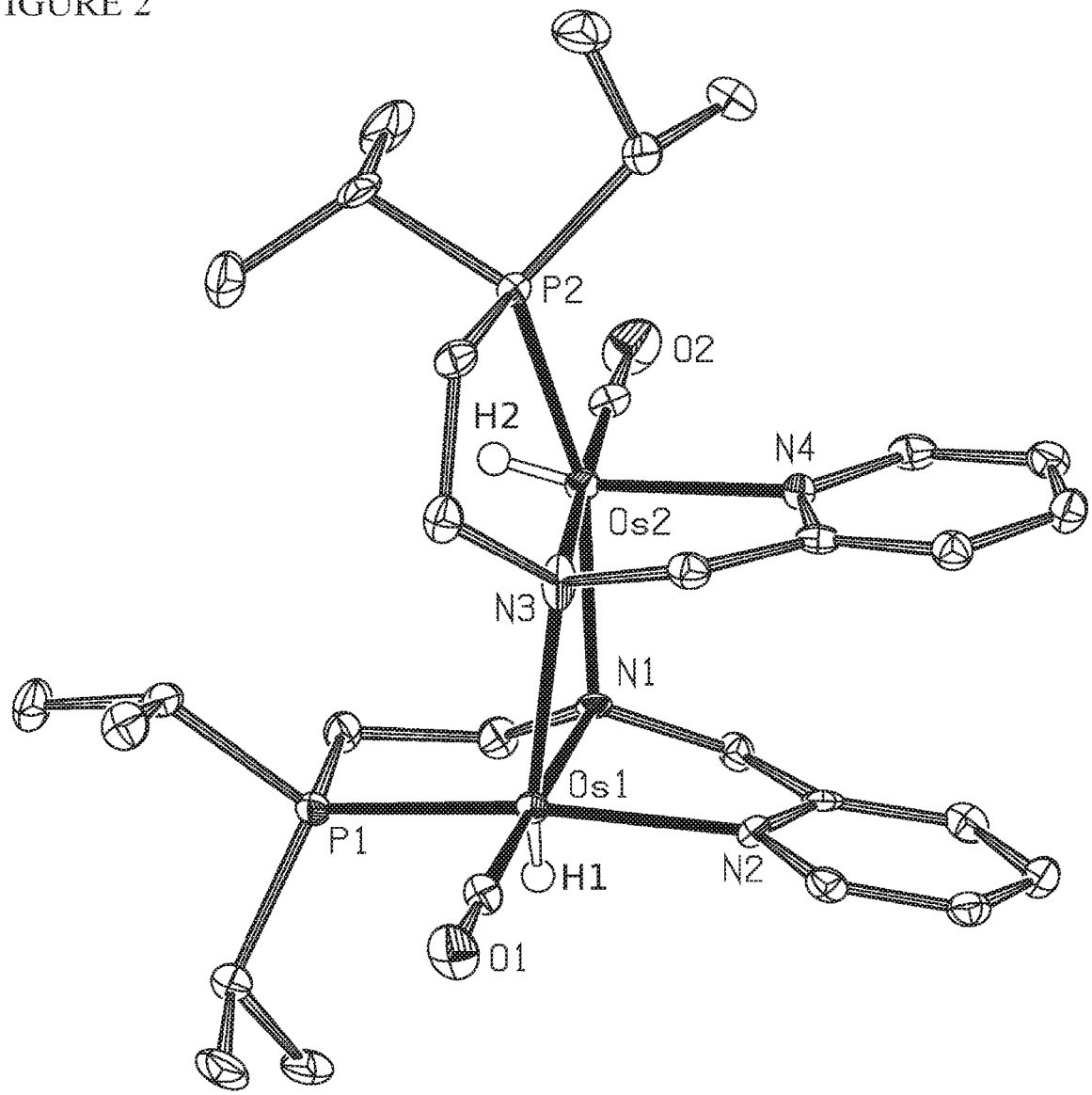
FIG. 2 is an ORTEP diagram for complex 2, thermal ellipsoids are at 50% probability (the hydrogen atoms are omitted for clarity).
Figure 3:
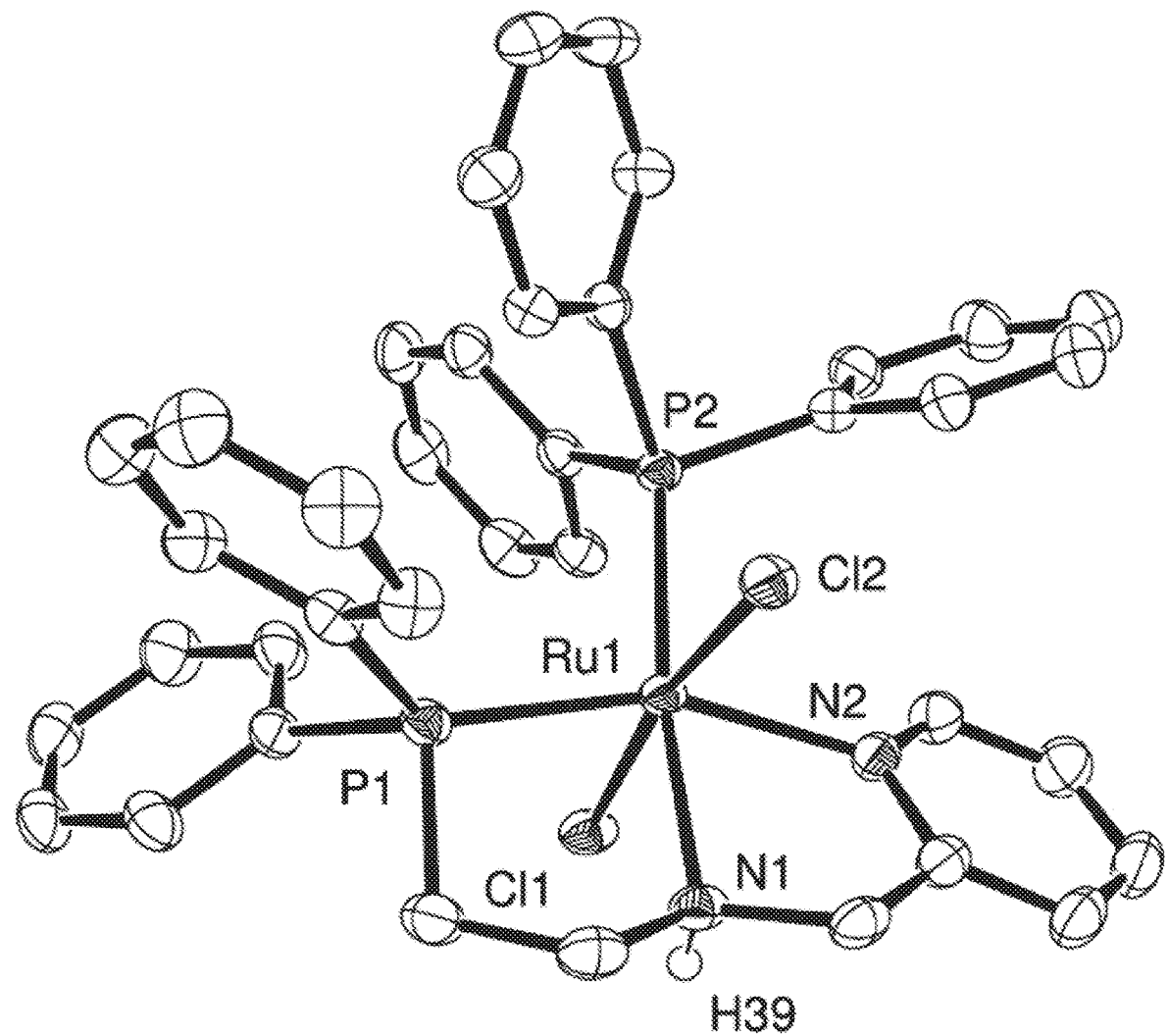
FIG. 3 is an ORTEP diagram for complex 7, thermal ellipsoids are at 50% probability (the hydrogen atoms except for NH are omitted for clarity).

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, "heteroatom" refers to non-hydrogen and non-carbon atoms, such as, for example, O, S, and N.

As used herein, "alkyl" means a hydrocarbon moiety that consists solely of single-bonded carbon and hydrogen atoms, for example a methyl or ethyl group.

As used herein, "alkenyl" means a hydrocarbon moiety that is linear, branched or cyclic and comprises at least one carbon to carbon double bond. "Alkynyl" means a hydrocarbon moiety that is linear, branched or cyclic and comprises at least one carbon to carbon triple bond. "Aryl" means a moiety including a substituted or unsubstituted aromatic ring, including heteroaryl moieties and moieties with more than one conjugated aromatic ring; optionally it may also include one or more non-aromatic ring. "$C_5$ to $C_8$ Aryl" means a moiety including a substituted or unsubstituted aromatic ring having from 5 to 8 carbon atoms in one or more conjugated aromatic rings. Examples of aryl moieties include phenyl.

"Heteroaryl" means a moiety including a substituted or unsubstituted aromatic ring having from 4 to 8 carbon atoms and at least one heteroatom in one or more conjugated aromatic rings. As used herein, "heteroatom" refers to non-carbon and non-hydrogen atoms, such as, for example, O, S, and N. Examples of heteroaryl moieties include pyridyl, furanyl and thienyl.

"Alkylene" means a divalent alkyl radical, e.g., $-C_fH_{2f}-$ wherein f is an integer. "Alkenylene" means a divalent alkenyl radical, e.g., —CHCH—.

"Substituted" means having one or more substituent moieties whose presence does not interfere with the desired reaction. Examples of substituents include alkyl, alkenyl, alkynyl, aryl, aryl-halide, heteroaryl, cycloalkyl (non-aromatic ring), Si(alkyl)$_3$, Si(alkoxy)$_3$, halo, alkoxyl, amino, alkylamino, alkenylamino, amide, amidine, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfonate, sulfamoyl, sulfonamide, nitro, nitrile, azido, heterocyclyl, ether, ester, silicon-containing moieties, thioester, or a combination thereof. The substituents may themselves be substituted. For instance, an amino substituent may itself be mono or independently disubstituted by further substituents defined above, such as alkyl, alkenyl, alkynyl, aryl, aryl-halide and heteroaryl cycloalkyl (non-aromatic ring).

As used herein, the term "$\mu^Y$" is used to indicate that a ligand is functioning as a bridging ligand, where a single atom bridges two metal atoms. The superscript "Y" denotes the atom bridging the two metal atoms. For example, the term "$\mu^N$" is used to indicate that a ligand (or ligands) in a complex includes a nitrogen atom that bridges two metal atoms.

The present application provides a catalyst that is useful in a process of catalytic hydrogenation (reduction). The process is useful in hydrogenation of, for example, $C_3$-$C_n$ (n=4-200) substrates possessing one or more ester or lactone groups to afford the corresponding alcohol, diol, or triol products. Thus, the present application further provides a practical reduction method that can be used in place of the main-group hydride reduction to obtain alcohols, diols, or triols in a simple, efficient, and "green" fashion, preferably using base-free reaction conditions. The catalyst of the present application is also useful in a process of catalytic dehydrogenation, which can be a homogeneous dehydrogenation process.

Catalyst

The processes described herein are carried out in the presence of a transition metal complex having a tridentate ligand LNN'.

In accordance with one aspect, there is provided a tridentate ligand LNN' comprising, in sequence, one phosphorus, sulfur, nitrogen or carbon group L, one amino or imino group N, and one heterocycle group N'.

In accordance with one embodiment, there is provided a compound of Formula I

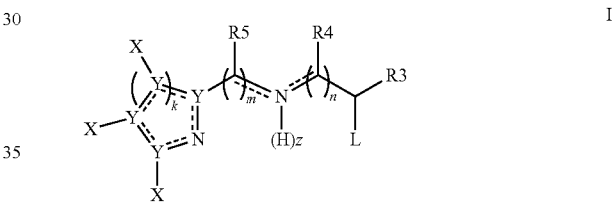

wherein

L is a phosphine (PR$^1$R$^2$), a sulfide (SR$^1$), or a carbene group (CR$^1$R$^2$);

each Y is independently a C, N or S atom, wherein at least two Y's are C;

the dotted lines simultaneously or independently represent single or double bonds;

R$^1$ and R$^2$ are each independently H, or a C$_1$-C$_{20}$ linear alkyl, a C$_3$-C$_{20}$ branched alkyl, a C$_3$-C$_8$ cycloalkyl, a C$_2$-C$_8$ alkenyl, a C$_5$-C$_{20}$ aryl, each of which may be optionally substituted; or when taken together, R$^1$ and R$^2$ can together with L to which they are bound form a saturated or partially saturated ring;

R$^3$ and R$^4$ are each independently H, or a C$_1$-C$_8$ linear alkyl, a C$_3$-C$_8$ branched alkyl, a C$_3$-C$_8$ cyclic alkyl, a C$_2$-C$_8$ alkenyl, a C$_5$-C$_8$ aryl, each of which may be optionally substituted; or R$^3$ and R$^4$ can join together to form a saturated heterocycle;

R$^5$ is H, a linear C$_1$-C$_8$ alkyl, a branched C$_3$-C$_8$ alkyl, a cyclic C$_3$-C$_8$ alkyl, a C$_2$-C$_8$ alkenyl, or a C$_5$-C$_8$ aryl, each of which can be optionally substituted; or R$^5$ and R$^4$ can join together to form a saturated heterocycle;

each X is independently H, a linear C$_1$-C$_8$ alkyl, a branched C$_3$-C$_8$ alkyl, a cyclic C$_3$-C$_8$ alkyl, a C$_2$-C$_8$ alkenyl, or a C$_5$-C$_8$ aryl, each of which can be optionally substituted, or OR, F, Cl, Br, I or NR$_2$; or when taken together, two of the X groups can together form an optionally substituted, saturated, partially saturated, aromatic or heteroaromatic ring;

R is H, a $C_1$-$C_{20}$ linear alkyl, a $C_3$-$C_{20}$ branched alkyl, a $C_3$-$C_8$ cycloalkyl, a $C_2$-$C_8$ alkenyl, or a $C_5$-$C_8$ aryl, each of which may be optionally substituted;

each n and m is independently 1 or 2;

k is 1 or 2;

and z is 0 or 1.

In accordance with one embodiment, $R^3$ and $R^4$ are each independently H, or $C_1$-$C_8$ linear alkyl, $C_3$-$C_8$ branched alkyl, cyclic alkyl $C_3$-$C_8$, $C_1$-$C_8$ alkenyl, $C_5$-$C_8$ aryl, each of which may be optionally substituted, or OR or $NR_2$; and $R^5$ is H, a linear $C_1$-$C_8$ alkyl, branched $C_3$-$C_8$ alkyl, cyclic $C_3$-$C_8$ alkyl, $C_3$-$C_8$ alkenyl, or $C_5$-$C_8$ aryl, each of which can be optionally substituted, or OR or $NR_2$. In one preferred embodiment, $R^4$ and $R^5$ are both H.

In accordance with another embodiment, each Y is C. In accordance with another embodiment, k is 2, and each X is H. In accordance with one preferred embodiment, L is a phosphene.

In accordance with one embodiment, the compound of Formula I is

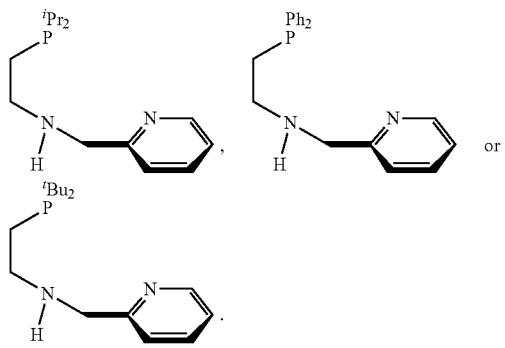

In accordance with another aspect, there is provided a complex of Formula II or III $$[M(LNN')Z_a] \qquad (II)$$

$$\mu^N[M(LNN')Z_a]_2 \qquad (III)$$

wherein:

each Z is independently a hydrogen or halogen atom, a $C_1$-$C_6$ alkyl, a hydroxyl, or a $C_1$-$C_6$ alkoxy, a nitrosyl (NO) group, CO, CNR, or $PR_3$, wherein R is an alkyl or an aryl, $PMe_3$ or $PPh_3$;

M is a transition metal; and each LNN' is a coordinated ligand that is a compound of any one of claims 1-7.

In accordance with one embodiment, M is a group 7 metal, a group 8 metal or a group 9 metal. In accordance with one preferred embodiment, M is Ru or Os.

In accordance with another embodiment, the complex comprises the ligand LNN', wherein LNN' is

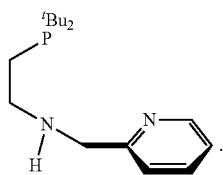

In accordance with another embodiment, the complex has the structure of

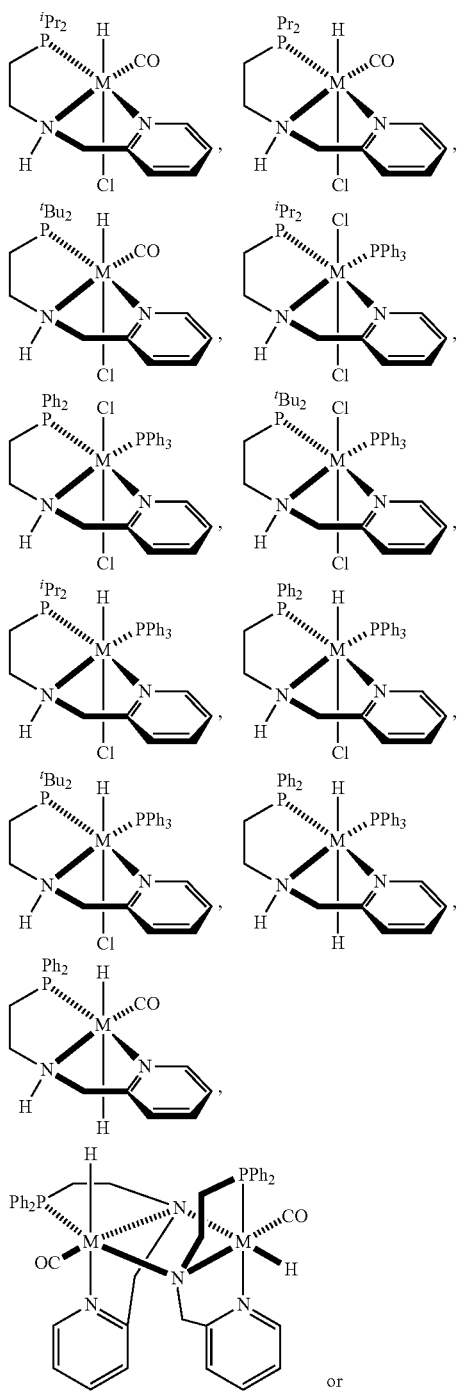

or

-continued

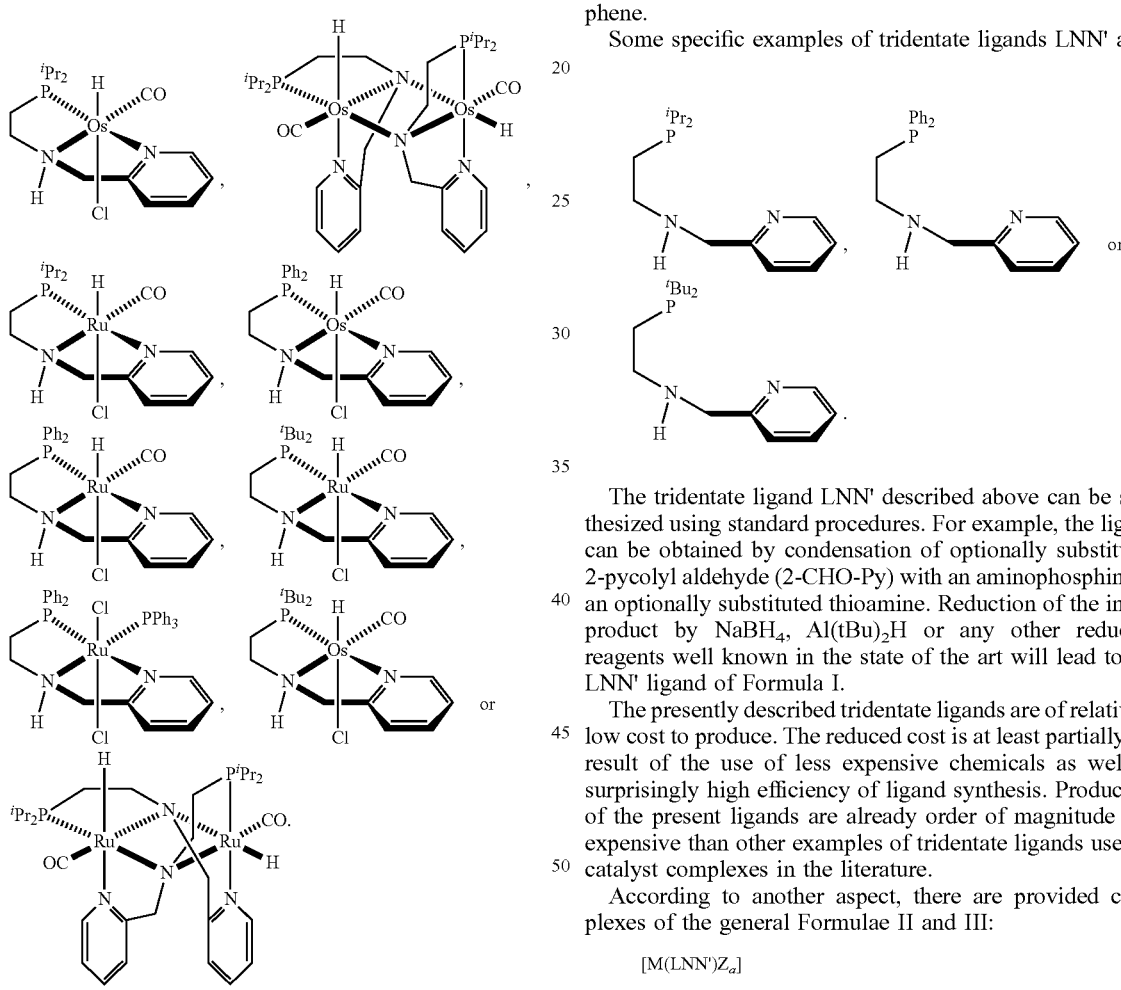

wherein M is as defined above.

In one preferred embodiment, the complex has the structure of any one of

In accordance with another aspect, there is provided a process for dehydrogenation of a substrate comprising treating the substrate with a catalytic amount of a complex as described. In one embodiment, the substrate is a compound of Formula IV

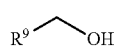   IV wherein $R^9$ is a $C_{1-20}$ linear alkyl, a $C_{3-20}$ branched alkyl, a $C_{3-20}$ cycloalkyl, or an aryl, any of which may be optionally substituted.

In accordance with another aspect, there is provided a tridentate ligand LNN' having formula I, $R^4$ is H, a substituted or unsubstituted linear, branched or cyclic $C_3$-$C_8$ alkyl or alkenyl, a substituted or an unsubstituted $C_5$-$C_8$ aromatic group, and $R^5$ is a substituted or unsubstituted linear, branched or cyclic $C_3$-$C_8$ alkyl or alkenyl, a substituted or unsubstituted $C_5$-$C_8$ aryl.

In one embodiment, the heterocycle group N' of Formula I, wherein k is 1 or 2, the nitrogen heterocycle N' is optionally substituted and contains carbon, nitrogen, oxygen, or sulfur atoms Y. One preferred example of the heterocycle N' is the $C_2$-pyridyl group, $C_5H_4N$.

In another particular embodiment, L is an N-heterocyclic carbene. In another particular embodiment, L is a phosphene.

Some specific examples of tridentate ligands LNN' are:

The tridentate ligand LNN' described above can be synthesized using standard procedures. For example, the ligand can be obtained by condensation of optionally substituted 2-pycolyl aldehyde (2-CHO-Py) with an aminophosphine or an optionally substituted thioamine. Reduction of the imine product by $NaBH_4$, $Al(tBu)_2H$ or any other reducing reagents well known in the state of the art will lead to the LNN' ligand of Formula I.

The presently described tridentate ligands are of relatively low cost to produce. The reduced cost is at least partially the result of the use of less expensive chemicals as well as surprisingly high efficiency of ligand synthesis. Production of the present ligands are already order of magnitude less expensive than other examples of tridentate ligands used in catalyst complexes in the literature.

According to another aspect, there are provided complexes of the general Formulae II and III:

$$[M(LNN')Z_a] \qquad \qquad II$$

$$\mu^N[M(LNN')Z_a]_2 \qquad \qquad III$$

wherein LNN' is the tridentate ligand of Formula I and a equals 2 or 3. Each Z represents simultaneously or independently a hydrogen or halogen atom, a $C_1$-$C_6$ alkyl radical, a hydroxyl group, or a $C_1$-$C_6$ alkoxy radical, a nitrosyl (NO) group, CO, CNR (R=Alkyl, Aryl), $PMe_3$ or $PPh_3$, and M is a transition metal. The complexes as presently described may exist in both neutral and cationic forms.

In accordance with one embodiment, the transition metal M is preferably a metal from groups 7 (manganese group), 8 (iron group), and 9 (cobalt group). In one preferred embodiment, the transition metal is Ru or Os.

In one embodiment, the complex of Formula II can be prepared by reaction of the LNN' ligand of Formula I with a metal precursor, such as those well known in the state of the art. Preferably, the metal precursor is a ruthenium or osmium compound, including, for example, the following formulae: $RuHCl(CO)(AsPh_3)_3$, $RuCl_2(CO)(AsPh_3)_3$, $RuHCl(CO)(PPh_3)_3$, $RuCl_2(CO)(PPh_3)_3$, $OsHCl(CO)(AsPh_3)_3$, $OsCl_2(CO)(AsPh_3)_3$, $OsHCl(CO)(PPh_3)$, $OsCl_2(CO)(PPh_3)_3$, $[RuCl_2(p\text{-cymene})]_2$, $[OsCl_2(p\text{-cymene})]_2$, $RuCl_2(CO)(p\text{-cymene})$, $OsCl_2(CO)(p\text{-cymene})$, $RuCl_2(CO)(DMF)(PPh_3)_2$, $[IrCl(COD)]_2$, $[IrCl(COE)_2]_2$, $IrHCl_2(PPh_3)_3$, $IrH_2Cl(PPh_3)_3$, $IrHCl_2(AsPh_3)_3$, or $IrH_2Cl(AsPh_3)_3$. The reactions can be conducted in various organic solvents, such as, but not limited to, toluene, xylene, benzene, diglyme, DMF or DME.

In accordance with another embodiment, transformation of a complexes of Formula II to a complex of Formula III can be achieved using a base. Non-limiting examples of suitable bases include group I salts (such as Li, Na, K) of alkoxides, such as t-butoxide, and amides, such as $N(TMS)_2$. One specific examples of an acceptable base is potassium t-butoxide. In certain, non-limiting, examples, the base has a pKa>11. Additional non-limiting examples of suitable bases are group I salts or ammonium of hydroxides, alcoholates, alkaline carbonates, amides, siliconates, hydrides, borohydrides, aluminum hydrides, where the group I salt is Li, Na, K, or ammonium salts of the formula $NR_4$, and R is alkyl, aryl or H.

Complexes of Formulae II and III can be prepared prior to hydrogenation or in situ using above bases. Preparation of complexes of Formula II and III can be performed in various solvents, such as, but not limited to THF, $Et_2O$, toluene, benzene, diglyme, DMF or DME or any other appropriate solvents known to the person skilled in the art.

Structures of exemplary complexes 1-9 are shown below:

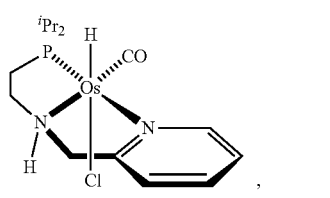
1

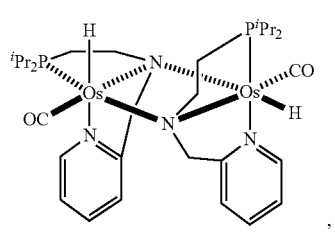
2

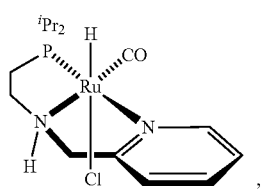
3

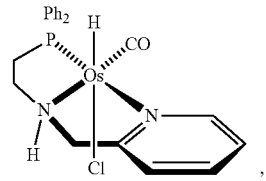
4

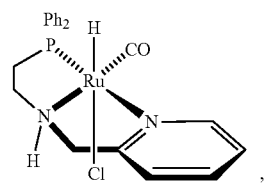
5

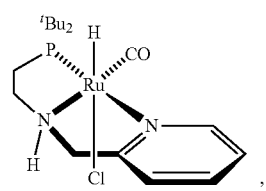
6

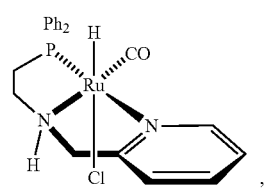
7

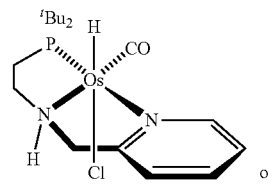
8
or

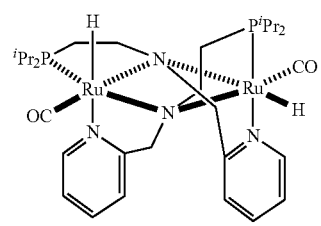
9

In another aspect, there is provided a process for making ethyl acetate comprising treating ethanol with a catalytic amount of a complex as described herein. In one embodiment, the process of is a homogeneous process. In another embodiment, the process does not require a hydrogen acceptor.

Hydrogenation Process

The present application additionally provides a catalytic hydrogenation process. The catalyst complexes of Formulae II and III described above, have been found to show high selectivity toward reduction of the ester groups in the presence of C=C double bonds. This provides a useful way of deriving unsaturated alcohols from natural products such as, but not limited to, olive or canola oils, under mild reduction conditions.

In one embodiment, there is provided a process for hydrogenation of esters using metal catalysts based on the LNN' ligand of Formula I. According to specific embodiment, the substrates are compounds of the following formulae:

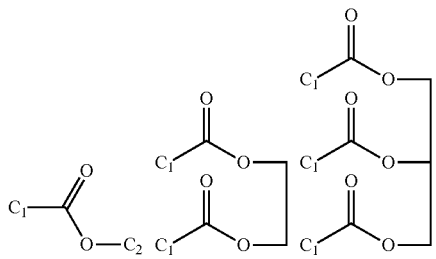

The term "substrate", as used herein and as commonly understood, refers to the reactant that will be converted to a product during a catalytic reaction. Groups G1 and G2, simultaneously or independently, represent a linear, branched $C_1$-$C_{40}$ or cyclic $C_3$-$C_{40}$ alkyl, alkenyl or aromatic group, optionally substituted. Also, one may cite a situation when G1 and G2 together form a $C_4$-$C_{40}$ saturated or an unsaturated radical. The substrate of the hydrogenation reaction can be any organic compound containing one, or more than one, carboalkoxy group. In this respect, natural fats such as olive, canola, corn, peanut, palm and other plant oils are useful substrates that can be reduced to form a mixture of alcohols.

The reduction or hydrogenation reaction proceeds, generally, according to the one of the reactions scheme below:

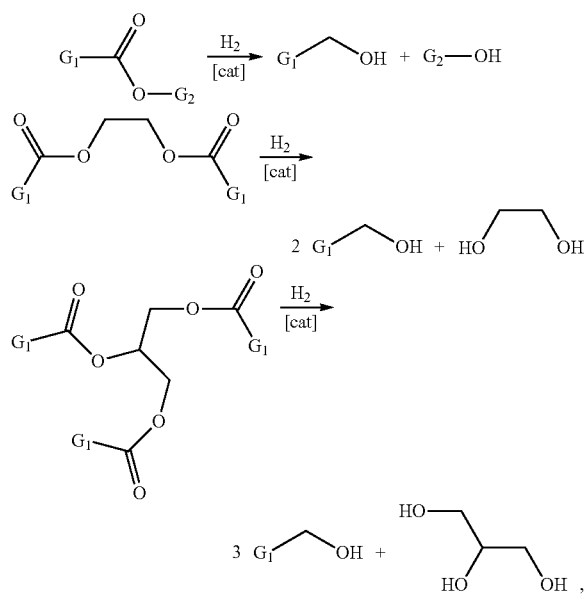

wherein $G_1$ and $G_2$ are independently selected from any optionally substituted hydrocarbon group. For clarity, where multiple substituents $G_1$ occur in the same molecule, it is understood that each of these substituents can be a different optionally substituted hydrocarbon.

When the substrate is a monoester or a lactone, the products are alcohols or a diol, respectively. The naturally occurring triglycerides, oils and fats, can be reduced to glycerol and the corresponding fatty alcohols.

According to one embodiment of the invention, the process of catalytic reduction of esters implies the usage of at least one of the metal complexes 1 or 2, hydrogen pressure, and optionally a base and a solvent. The base may be necessary in those cases when the metal catalyst 1 contains one or more halogen atoms bonded to the metal. The treatment with base can be done prior to the reduction or in situ by adding base to the reaction mixture during hydrogenation. The catalysts and pre-catalysts of this invention can be used in a wide range of concentration, preferably between 10-1000 ppm, and the loadings of 500 ppm or less are particularly preferred. The preferred amount of the catalyst will depend, as it is known to the person skilled in the art, on the type of the substrate, and increasing the catalyst loading should result in faster hydrogenation. The temperature at which the hydrogenation can be carried out is comprised between 0° C. and 150° C., more preferably in the range between 50° C. and 100° C. and, as it is known to the person skilled in the art, the reaction rate will increase with increase of the reaction temperature. The hydrogenation reaction needs a pressure of $H_2$ gas and should be performed in a suitable pressure vessel. The surface area of the reactor as well as the hydrogen pressure, as it is known to the person skilled in the art, can greatly influence the reaction rate. The greater are the hydrogen pressure and the surface area of the reactor, the faster is the hydrogenation reaction rate. One may cite the hydrogen pressure in range of 10-200 Bar. Again, the person skilled in the art is well able to adjust the pressure as a function of the catalyst load and of the dilution of the substrate in the solvent. As examples, one can cite typical pressures of 5 to 50 bar (5 to 50×10 Pa).

It should be well understood, however, that the catalyst complexes described herein are also useful in catalyzing hydrogenation of substrates including functional groups other than esters. The table below provides a non-limiting list of substrates and corresponding products that can be formed from a catalytic hydrogenation reaction using a catalyst of Formula II or III.

| Hydrogenation Substrate | Product |
| --- | --- |
| aldehyde | alcohol |
| ketone | alcohol |
| ester | alcohol |
| carboxylic acid | alcohol |
| ketene | alcohol |
| enol | alcohol |
| epoxide | alcohol |
| aldimine | amine |
| ketimine | amine |
| ketene-imine | amine |
| nitrile | amine |
| aziridine | amine |
| nitro | amine |
| diazo | amine |
| isocyanide | amine |
| enamine | amine |
| lactone | diol |
| amide | amine + alcohol |
| aminoboranes | amine-borane |
| borazine | amine-borane |
| olefin | alkane |
| acetylene | alkane |
| allene | alkane |

Dehydrogenation Reaction

The present application further provides a process of catalytic dehydrogenation using the catalyst complexes of Formulae II and III. For example, this catalyst or precatalyst is suitable for dehydrogenation of $C_2$-$C_n$ (n=4-200) alcohols possessing one or more —$CH_2OH$ groups thereby affording hydrogen gas and the corresponding esters or lactons, according to the following scheme. In one embodiment this process is a homogeneous dehydrogenation process, that can be used in place of the existing heterogeneous techniques, preferably using base-free reaction conditions and avoiding high reaction temperatures.

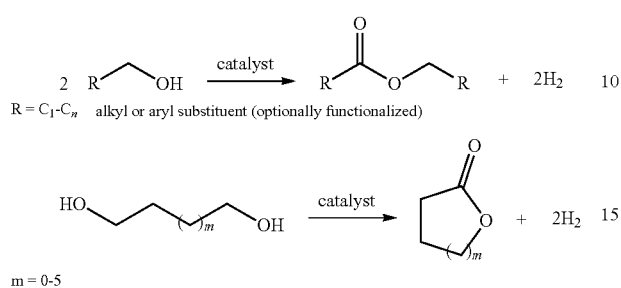

Accordingly, one embodiment provides a process for dehydrogenation of alcohols using metal catalysts based on the LNN' ligand of Formula I. According to an embodiment of the invention, the substrates are compounds of the following formulae:

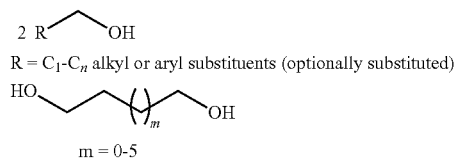

In this embodiment, R groups, simultaneously or independently, represent a linear, branched $C_1$-$C_{40}$ or cyclic $C_3$-$C_{40}$ alkyl, alkenyl or aromatic group, optionally substituted. Also, one may cite a situation when R is $C_4$-$C_{40}$ saturated or an unsaturated cyclic radical. This implies that the substrate can be any organic compound containing one, or more than one, hydroxyl (—OH) group. When the substrate is an alcohol or diol, the products are an ester or a lactone, respectively.

According to one embodiment, the process of catalytic acceptorless dehydrogenation implies the usage of at least one of the metal complexes of Formulae II or III and (optionally) the use of a base and a solvent. The base may be necessary in those cases when the metal catalyst of Formula II contains one or more halogen or alkoxy (—OR) groups bonded to the metal. The catalyst can be treated with base prior to mixing with the substrate or in situ by adding base to the reaction mixture during dehydrogenation. The catalysts and pre-catalysts described herein can be used in a wide range of concentration, preferably between 10-1000 ppm, and the loadings of 1000 ppm or less are particularly preferred. The preferred amount of the catalyst will depend, as it is known to the person skilled in the art, on the type of the substrate; and increasing the catalyst loading should result in faster dehydrogenation. The temperature at which the dehydrogenation can be carried out is comprised between 0° C. and 200° C., more preferably in the range between 50° C. and 150° C. and, as it is known to the person skilled in the art, the reaction rate will increase with increase of the reaction temperature. The dehydrogenation process can generate a pressure of $H_2$ gas and, in such case, can be performed in a suitable pressure vessel, if necessary equipped with a pressure-release valve.

It should be well understood, however, that the catalyst complexes described herein are also useful in catalyzing dehydrogenation of substrates including functional groups other than alcohols. The table below provides a non-limiting list of substrates and corresponding products that can be formed from a catalytic dehydrogenation reaction using a catalyst of Formula II or III.

| Substrate | Product[a] |
| --- | --- |
| alcohols | ester |
| alcohol | aldehyde |
| alcohol | ketone |
| diol | lactone |
| amine + alcohol | amide |
| amine + alcohol | substituted amine |
| amine + alcohol | imine |
| ammonia-borane | aminoboranes |
| ammonia-borane | borazine |
| amine | imine |
| amines | guanidine |
| alcohol + thiol | thioester |
| thiol | sulphoxide |
| alcohol + phosphine | acyl phosphine |

[a]$H_2$ is also a byproduct of these reactions, it is either liberated from the reaction as $H_2$ or transferred to an acceptor.

As noted above, a byproduct of the dehydrogenation reactions is $H_2$. Accordingly, the present application further provides a process for producing $H_2$. The process can conveniently make use of readily available substrates in a straightforward catalytic dehydrogenation process under relatively mild conditions to generate $H_2$.

To gain a better understanding of the invention described herein, the following examples are set forth. It should be understood that these examples are for illustrative purposes only. Therefore, they should not limit the scope of this invention in any way.

EXAMPLES

Unless mentioned otherwise, all manipulations were performed under an inert gas (argon or nitrogen) in gloveboxes or using standard Schlenk techniques. NMR spectra were recorded on a Varian Unity Inova 300 MHz spectrometer. All $^{31}P$ chemical shifts are relative to 85% $H_3PO_4$. $^1H$ and $^{13}C$ chemical shifts were measured relative to the solvent peaks but are reported relative to TMS. $OsO_4$ and $RuCl_3 \cdot 3H_2O$ were purchased from Pressure Chemicals. All other chemicals and anhydrous grade solvents were obtained from Aldrich and Alfa Aesar. Commercial anhydrous grade ethanol was further distilled over sodium metal and stored in the argon glovebox. $(NEt_4)_2OsCl_6$, $RuHCl(CO)(AsPh_3)_3$, $OsHCl(CO)(AsPh_3)_3$, $RuCl_2(PPh_3)_3$, $RuCl_2(CO)(DMF)$ $(PPh_3)_2$ were prepared according to previously reported methods. (Gusev, D. G., Dolgushin, F. M., Antipin, M. Yu. Organometallics 2001, 20, 1001; Spasyuk, D., Smith, S., Gusev, D. G. Angew. Chem. 2012, 51, 2772-2775; Shaw, A. P., Ryland, B. L., Norton, J. R., Buccella, D., Moscatelli, A. Inorg. Chem. 2007, 46, 5805-5812; Rajagopal, S., Vancheesan, S., Rajaram, J., Kuriacose, J. C. J. Mol. Cat. 1983, 22, 131-135, all incorporated herein by reference.)

Example 1—Synthesis of $PyCH_2NH(CH_2)_2N(iPr)_2$ 2-aminoethyl diisopropylamine (6.32 g, 0.044 mmol) was added to 2-picolyl aldehyde (4.70 g, 0.044 mmol) and the mixture was stirred for 1 h. The obtained imine was diluted with methanol (15 mL) and $NaBH_4$ (1.66 g, 0.044 mmol)

was added portion-wise during 1 h. Then, all volatiles were removed under vacuum, and the residue was re-dissolved in 20 mL of dichloromethane. The solution was filtered through a short pad (3×2 cm) of $Al_2O_3$. The aluminum oxide was then washed with 10 mL of dichloromethane and the collected filtrate was evaporated and dried under vacuum for 1 h. The product was obtained as a yellow oil (8.41 g, 90%).

$^1$H NMR (300 MHz, $CDCl_3$) δ=8.47 (ddd, J=4.8, 1.8, 0.9 Hz, 1H), 7.73 (td, J=7.6, 1.8 Hz, 1H), 7.39 (d, J=7.8 Hz, 1H), 7.21 (ddd, J=7.5, 4.9, 1.2 Hz, 1H), 3.77 (s, 2H), 3.33 (br., 1H, NH), 2.97 (sep, J=7.0, 2H; CH), 2.48 (m, J=2.5 Hz, 4H, $CH_2$), 0.92 (d, J=6.6 Hz, 12H; 4×$CH_3$).

$^{13}$C NMR ([D6]DMSO) δ=160.62 (s, 1C; Py), 148.75 (s, 1C; Py), 136.33 (s, 1C; Py), 121.75 (s, 1C; Py), 121.65 (s, 1C; Py), 54.71 (s, 1C; $CH_2$), 49.23 (s, 1C; $CH_2$), 47.65 (s, 2C; CH), 44.14 (s, 1C; $CH_2$), 20.72 (s, 1C; 4×$CH_3$).

Example 2—Synthesis of $PyCH_2NH(CH_2)_2P(iPr)_2$ 2-picolyl aldehyde (1.66 g, 0.0155 mmol) in 10 mL of THF was added to a 10 wt % solution of 2-(di-i-propylphosphino)ethylamine in THF (26.0 g, 0.0162 mmol) and the mixture was stirred for 1 h. The obtained imine was then treated with diisobutyl aluminum hydride (22.7 mL, 1.5 M in toluene, 0.0341 mmol) during 1 h (Caution!!! Exothermic reaction!) and left to stir for 1 h. After that time, the solution was quenched with 1 mL of water (Caution!!! Exothermic reaction!) and the obtained suspension was filtered through a short pad (3×2 cm) of basic alumina. The solids were washed with THF (3 ? 10 mL) and the collected filtrate was evaporated and dried under vacuum for 3 h. The product was obtained as a yellow oil (2.84 g, 73%).

$^{31}$P {$^1$H} NMR ([D6]Benzene) δ=−1.0 (s). $^1$H NMR ([D6]Benzene) δ=8.49 (dt, J=4.7, 1.8 Hz, 1H; Py), 7.15-7.13 (m, 1H; Py), 7.09 (td, J=7.7, J=1.8 Hz, 1H; Py), 6.64 (ddd, J=7.0, 4.9, 1.7 Hz, 1H; Py), 3.93 (s, 2H; $PyCH_2$), 2.81 (m, 2H; $NCH_2$), 1.78 (br. s, 1H; NH), 1.65-1.35 (m, 4H; $PCH_2$ and $CH_2P$), 1.01 (dd, J=13.8, 7.1 Hz, 6H; $CH_3$), 0.96 (dd, J=10.8, 7.0 Hz, 6H; $CH_3$). $^{13}$C {$^1$H} NMR ([D6]Benzene) δ=161.37 (s, 1C; Py), 149.49 (s, 1C; Py), 135.85 (s, 1C; Py), 121.92 (s, 1C; Py), 121.60 (s, 1C; Py), 55.72 (s; 1C; $NCH_2$), 49.12 (d, J(CP)=24.9 Hz, 1C; $NCH_2$), 23.72 (d, J(CP)=13.5 Hz, 2C; $PCH$), 23.37 (d, J(CP)=19.3 Hz, 1C; $PCH_2$), 20.29 (d, J(CP)=16.5 Hz, 2C; $CH_3$), 18.93 (d. J(CP)=9.9 Hz, 2C; $CH_3$).

Example 3—Synthesis of trans-OsHCl(CO)[$PyCH_2NH(CH_2)_2P(iPr)_2$]

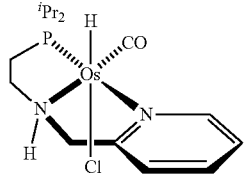

Complex 1

A flask containing a mixture of $OsHCl(CO)(AsPh_3)_3$ (5.94 g, 5.57 mmol) and $PyCH_2NH(CH_2)_2P(iPr)_2$ (1.27 g, 5.06 mmol) in 15 mL of diglyme was placed in a preheated to 160° C. oil bath and stirred for 1 h, affording a dark-red solution. After cooling to room temperature, the mixture was diluted with 4 mL of diethylether, and the flask was stored overnight in a freezer at 18° C. The precipitated product was filtered off, washed with diethyl ether (3×3 mL), and dried under vacuum for 3 h to give a brown crystalline solid. Yield: 1.81 g (71%).

$^{31}$P {$^1$H} NMR ([D2]DCM) δ=48.41 (s). $^1$H {$^{31}$P} NMR ([D2]DCM) δ=9.00 (d, J=5.5 Hz, 1H, Py), 7.68 (td, J=7.8, 1.5 Hz, 1H, Py), 7.28-7.16 (m, 1H, Py), 4.61 (dd, J=14.3, 4.4 Hz, 1H, $PyCH_2$), 4.12 (br. t, J=12.0 Hz, 1H, NH), 3.93 (dd, J=14.2, 11.6 Hz, 1H, $PyCH_2$), 3.67-3.58 (m, 1H, $NCH_2$), 2.73-2.53 (m, 1H, $NCH_2$), 2.46 (sep, J=14.7, 7.4 Hz, 1H, PCH), 2.37 (dd, J=15.0, 4.0 Hz, 1H, $CH_2P$), 2.11 (sept, J=6.9 Hz, 1H, PCH), 1.77 (td, J=14.6, 5.8 Hz, 1H, $CH_2P$), 1.35 (d, J=7.4 Hz, 3H, $CH_3$), 1.21 (d, J=7.2 Hz, 3H, $CH_3$), 1.09 (d, J=6.9 Hz, 3H, $CH_3$), 1.04 (d, J=7.0 Hz, 3H, $CH_3$), −16.45 (s, 1H, OsH, satellites J(OsH)=95.22). $^{13}$C {$^1$H} NMR ([D2]DCM) δ=188.57 (d, J(CP)=8.6 Hz, CO), 161.56 (s, 1C, Py), 153.89 (d, J(CP)=1.7 Hz, 1C; Py), 136.16 (s, 1C; Py), 125.13 (d, J(CP)=2.0 Hz, 1C; Py), 121.80 (d, J(CP)=1.7 Hz, 1C; Py), 60.62 (d, J(CP)=2.3 Hz, 1C; $CH_2$), 54.96 (d, J(CP)=1.7 Hz, 1C; $CH_2$), 33.07 (d, J(CP)=25.9 Hz, 1C; CH), 29.19 (d, J(CP)=30.3 Hz, 1C; CH), 26.03 (d, J(CP)=33.1 Hz, 1C; $CH_2$), 21.04 (d, J(CP)=3.9 Hz, 1C; $CH_3$), 20.57 (d, J(CP)=3.4 Hz, 1C; $CH_3$), 19.05 (s, 1C; $CH_3$), 17.51 (d, J(CP)=4.6 Hz, 1C; $CH_3$). IR (Nujol): $\nu_{C=O}$=1879 (s) Anal. Calc'd for $C_{15}H_{27}ClN_2OOsP$: C, 35.53; H, 5.17; N, 5.24. Found: C, 35.35; H, 5.19; N, 5.24.

Example 4—Synthesis of $\mu^N$-mer,fac-{OsH(CO)[$PyCH_2N(CH_2)_2P(iPr)_2$]}$_2$

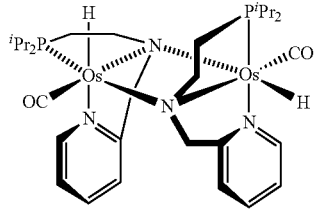

Complex 2

A mixture of $OsHCl(CO)[PyCH_2NH(CH_2)_2P(iPr)_2]$ (1.00 g, 1.97 mmol) and KOtBu (243 mg, 2.17 mmol) in 7 mL of THF was stirred for 2 h, then the resulting solution was placed in a freezer for 1 h. The red reaction mixture was filtered into a 20 mL vial, and 1 mL of THF was used to rinse the fritted funnel. The solution was diluted with 6 mL of diethyl ether and the compound was crystallized in a freezer at −18° C. The crystalline bright-yellow product was isolated by filtration and dried under vacuum for 1 h. Yield: 621 mg (67%).

$^{31}$P NMR ([D2]DCM) δ=67.73 (s), 51.50 (s). $^1$H {$^{31}$P} NMR ([D2]DCM) δ=8.86 (t, J=6.7 Hz, 2H, Py), 7.08 (t, J=7.8 Hz, 1H, Py), 7.01 (t, J=7.6 Hz, 1H, Py), 6.86-6.73 (m, 2H, Py), 6.34 (d, J=8.0 Hz, 1H, Py), 6.24 (d, J=7.8 Hz, 1H, Py), 5.24 (d, J=17.8 Hz, 1H, $PyCH_2$), 4.72 (d, J=19.4 z, 1H, $PyCH_2$), 4.14 (d, J=17.7 Hz, 1H, $NCH_2$), 3.84 (t, =12.9 Hz, 1H, $NCH_2$), 3.80-3.68 (m, 1H), 3.56-3.33 (m, 3H), 2.75 (hept, J=14.4, 1H; CH), 2.39-2.17 (m, 2H), 2.05 (hept, J=5.6, 1H, PCH), 1.99-1.87 (m, 1H), 1.83-1.62 (m, 1H), 1.32 (2d overlapped, J=−7.4 Hz, 3H), 1.28-1.16 (m, 1H), 1.09 (d, J=6.9 Hz, 3H; $CH_3$), 1.05 (d, J=6.8 Hz, 3H; $CH_3$), 0.95 (d, J=6.7 Hz, 3H; $CH_3$), 0.89 (d, J=6.9 Hz, 3H; $CH_3$), 0.73 (d, J=7.0 Hz, 3H; $CH_3$), 0.58 (t, J=7.3 Hz, 3H), −11.54 (s, 1H; OsH), −14.31 (s, 1H; OsH). $^{13}$C {$^1$H} NMR ([D2]DCM) δ=191.26 (d, J(CP)=9.0 Hz, 1C; CO), 190.06 (d, J(CP)=6.7

Hz, 1C; CO), 171.19 (s, 1C; Py), 170.65 (s, 1C; Py), 151.05 (s, 1C; Py), 150.77 (s, 1C; Py), 133.61 (s, 1C; Py), 133.36 (s, 1C; Py), 122.96 (d. J(CP)=2.0 Hz, 1C; Py), 122.80 (s, 1C; Py), 117.82 (s, 1C; Py), 75.84 (s, 1C; PyCH$_2$), 74.06 (s, 1C; PyCH$_2$), 70.28 (d, J(CP)=6.5 Hz, 1C; NCH$_2$), 68.89 (s, 1C; NCH$_2$), 36.42 (d, J(CP)=28.7 Hz, 1C; CH), 30.73 (d, J(CP)=21.3 Hz, 1C; CH), 29.15 (d, J(CP)=36.4 Hz, 1C; CH), 28.59 (d, J(CP)=21.8 Hz, 1C; CH), 26.46 (d, J(CP)=22.2 Hz, 1C; CH$_2$), 26.01 (d, J(CP)=32.2 Hz, 1C; CH$_2$), 22.32 (d, J(CP)=3.6 Hz, 1C; CH$_3$), 20.91 (d, J(CP)=4.7 Hz, 1C; CH$_3$), 20.17 (d, J(CP)=2.3 Hz, 1C; CH$_3$), 19.77 (s, 1C; CH$_3$), 19.58 (d, J(CP)=2.3 Hz, 1C; CH$_3$), 19.09 (s, 1C; CH$_3$), 18.26 (s, 1C; CH$_3$), 16.77 (d, J(CP)=7.0 Hz, 1C; CH$_3$).

Example 5—Synthesis of RuHCl(CO)(AsPh$_3$)$_3$

A 250 mL round-bottom Schlenk flask was loaded in air with RuCl$_3$.3H$_2$O (1.26 g, 4.85 mmol), AsPh$_3$ (5.94 g, 19.4 mmol), NEt(iPr)$_2$ (5.00 g, 38.7 mmol), 2-methoxyethanol (115 mL) and aqueous formaldehyde (40%, 15 mL). The stoppered flask was briefly opened to vacuum and refilled with argon; this procedure was repeated five times. The stirred reaction mixture was heated in an oil bath for 4 h while maintaining the bath temperature at 125° C. The resulting greyish suspension was left at room temperature for 1 h. The precipitate was filtered off, washed with ethanol (3×5 mL), and dried under vacuum for 2 h to give an off-white solid. Yield: 3.14 g (66%).

Example 6—Synthesis of trans-RuHCl(CO)[PyCH$_2$NH(CH$_2$)$_2$P(iPr)$_2$]

Complex 3

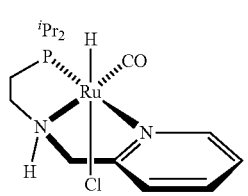

A 25 mL Schlenk flask containing a mixture of RuHCl(CO)(AsPh$_3$)$_3$ (2.13 g, 2.18 mmol) and PyCH$_2$NH(CH$_2$)$_2$P(iPr)$_2$ (500 mg, 1.98 mmol) in 20 mL of toluene was stirred under reflux for 1 h at 110° C. affording a dark brown solution. After cooling to room temperature, the product was filtered giving a pale brown powdery solid that was washed with diethylether (2×5 mL) and dried under vacuum. Yield: 671 mg (81%).

$^{31}$P {$^1$H} NMR ([D2]DCM) δ=94.74 (s). $^1$H {$^{31}$P} NMR ([D2]DCM) δ=8.93 (d, J=5.3 Hz, 1H; Py), 7.68 (td, 0.1=7.7, 1.6 Hz, 1H; Py), 7.32-7.12 (m, 2H; Py), 4.41 (d, 0.1-10.2 Hz, 1H; CH$_2$), 4.20-3.95 (m, 2H; NH+CH$_2$), 3.57-3.40 (m, 1H; CH$_2$), 2.62 (ddd, J=11.3, 9.3, 3.9 Hz, 1H; CH$_2$), 2.50 (sep, J=-7.1 Hz, 1H; CH), 2.30 (dd, J=15.0, 3.8 Hz, 1H; CH$_2$), 2.19 (sep, J=6.9 Hz, 1H; CH), 1.91 (td, J=14.6, 5.9 Hz, 1H; CH$_2$), 1.38 (d, J=7.4 Hz, 3H; CH$_3$), 1.21 (d, J=7.2 Hz, 3H; CH$_3$), 1.15-1.01 (overlapped d, 6H; 2CH$_3$), −14.93 (s, 1H; RuH). $^{13}$C {$^1$H} NMR ([D2]DCM) δ=206.52 (dd due to coupling to $^{31}$P and the residual coupling to the hydride, J(CP)=15.3, 7.3 Hz, 1C; CO), 160.91 (s, 1C; Py), 153.65 (d, J(CP)=1.3 Hz, 1C; Py), 136.79 (s, 1C; Py), 124.42 (d, J(CP)=2.0 Hz, 1C; Py), 121.57 (d, J(CP)=1.5 Hz, 1C; Py), 59.80 (s, 1C; PyCH$_2$), 52.98 (s, 1C; NCH$_2$), 32.58 (d, J(CP)=21.3 Hz, 1C; PCH$_2$), 29.02 (d, J(CP)=24.9 Hz, 1C; CH), 25.03 (d, J(CP)=28.5 Hz, 2C; CH), 20.69 (d, J(CP)=4.2 Hz, 2C; 2×CH$_3$), 19.05 (s, 1C; CH$_3$), 17.61 (d, J(CP)=5.2 Hz, 1C; CH$_3$).

Example 7—Hydrogenation of Esters Using Complexes 1 tBuOK (15 mg, 0.13 mmol) was added to a solution of complex 1 (51 mg, 0.10 mmol) in 10 mL of THF and the mixture was stirred for 3 min. 1 mL of the obtained solution was mixed with methyl benzoate (2.72 g, 20.0 mol) or other desired substrate in 6 mL of THF or toluene. The mixture was then placed into a 75 mL stainless-steel reactor (Parr 4740) equipped with a magnetic stir bar. The reactor was purged by two cycles of pressurization/venting with H$_2$ (150 psi, 10 Bar) and then pressurized with H$_2$ (725 psi, 50 Bar) and disconnected from the H$_2$ source. The reaction was conducted for 1.5 h at 100° C. in a preheated oil bath. At the end of the reaction time, the reactor was placed into a cold water bath and it was depressurized after cooling to the ambient temperature. The product benzyl alcohol was obtained after evaporation of all volatiles (THF, CH$_3$OH) under vacuum. The results are shown in tables 1-4 below. See table 2 for a complete list of tested substrates.

TABLE 1

Hydrogenation of methyl benzoate catalyzed by complexes 1-3, 7 and 9[a]

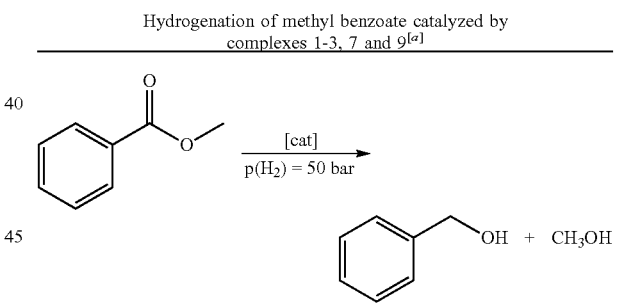

| Entry | Catalyst | Ester/[M][b] | T, ° C. | Time, h | Conv., % |
|---|---|---|---|---|---|
| 1 | 1[c] | 2000 | 100 | 1.5 | 100 |
| 2 | 2 | 2000 | 40 | 22 | 28 |
| 3 | 2 | 2000 | 60 | 7 | 82 |
| 4 | 2 | 2000 | 80 | 2.2 | 76 |
| 5 | 2 | 2000 | 100 | 1.5 | 99 |
| 6 | 2 | 3000 | 100 | 3 | 100 |
| 7 | 2 | 10000[d] | 100 | 19 | 80 |
| 8 | 3[c] | 2000 | 100 | 1.7 | 100 |
| 9 | 9 | 2000 | 40 | 17 | 82 |
| 10 | 9 | 2000 | 60 | 2.2 | 71 |
| 11 | 9 | 2000 | 80 | 1.2 | 88 |
| 12 | 9 | 2000 | 100 | 1 | 99 |
| 13 | 9 | 10000 | 100 | 14 | 100 |
| 14 | 9 | 20000 | 100 | 17 | 90 |
| 15 | 7 | 4000 | 40 | 16 | 98 |

[a]20 mmol of PhCOOMe in 7 mL of THF was hydrogenated in a 75 mL Parr pressure vessel.
[b]Substrate to metal molar ratio.
[c]With 1 mol % of tBuOK.
[d]120 mmol of PhCOOME, in a 300 mL vessel.

TABLE 2

Hydrogenation of esters (A-J) and imines (K, L) that afforded the corresponding alcohols and amines, catalyzed by complexes 2, 7 and 9[a].

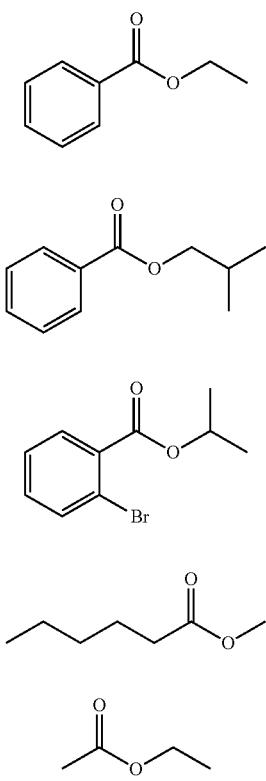

| Entry | Ester | Catalyst | Ester/[M][b] | Temp., °C | Time, h | Conv., % |
|---|---|---|---|---|---|---|
| 1 | A | 2 | 2000 | 100 | 1.6 | 99 |
| 2 | B | 2 | 2000 | 100 | 1.5 | 93 |
| 3 | C | 2 | 2000 | 100 | 17 | 0 |
| 4 | D | 2 | 2000 | 100 | 2 | 100 |
| 5 | D | 2[c] | 3000 | 100 | 2.7 | 100 |
| 6 | D | 9 | 2000 | 100 | 1.5 | 93 |
| 7 | D | 9 | 10000 | 100 | 18 | 71 |
| 8 | D | 7[d] | 20000 | 40 | 18 | 94 |
| 9 | E | 2 | 2000 | 100 | 3 | 100 |
| 10 | E | 7[e] | 20000 | 40 | 16 | 100 |
| 11 | F | 2 | 2000 | 100 | 1.4 | 99 |
| 12 | F | 9 | 2000 | 100 | 5 | 67 |
| 13 | G | 2 | 2000 | 100 | 9 | 72 |
| 14 | G | 7[f] | 2000 | 40 | 16 | 98 |
| 15 | H | 2 | 2000 | 100 | 21 | 0 |
| 16 | I | 9 | 2000 | 100 | 5.7 | 85 |
| 17 | J | 7[g] | 4000 | 40 | 16 | 100 |
| 18 | K | 7[g] | 50000 | 40 | 16 | 100 |
| 19 | L | 7[g] | 2000 | 40 | 16 | 100 |

[a]20 mmol of substrate in 7 mL of THF was hydrogenated in a 75 mL pressure vessel under p(H$_2$) = 50 Bar.
[b]Substrate to metal molar ratio.
[c]120 mmol of substrate, using a 300 mL vessel.
[d]With 5 mol % of KOMe.
[e]With 1 mol % of NaOEt.
[f]With 10 mol % of KOMe.
[g]With 1 mol % of tBuOK.

TABLE 3-continued

Exemplary Substrate-Product pairs

| Substrate | Product |
|---|---|
| methyl methoxyacetate (MeO-CH2-C(O)-OMe) | 2-methoxyethanol (MeO-CH2-CH2-OH) + MeOH |
| methyl (S)-lactate | (S)-propane-1,2-diol + MeOH |
| N-phenyl benzaldimine (PhCH=N-Ph) | N-benzylaniline (PhCH2-NH-Ph) |
| N-propyl benzaldimine (PhCH=N-nPr) | N-benzylpropylamine (PhCH2-NH-nPr) |

TABLE 4

Hydrogenation of fatty esters catalyzed by complexes 2, 3 and 9[a]

$$\text{[cat]}, R\overset{O}{\underset{}{\|}}C-OR'/[M]$$

| Substrate | [cat], R'/[M] | Product | Conversion |
|---|---|---|---|
| methyl (E)-non-2-enoate | 2, 2000 / THF, 16 h | methyl nonanoate | 100% |
|  | 3[a], 2000 / THF, 16 h | nonan-1-ol | 100% |
| methyl (E)-non-2-enoate | 2, 2000 / THF, 6 h | (E)-non-2-en-1-ol | 100% |
|  |  | N/R | 0% |
| methyl oleate (C8H17-CH=CH-(CH2)7-C(O)-OMe) | 2, 2000 / THF, 4 h | (Z)-octadec-9-en-1-ol (C8H17-CH=CH-(CH2)8-OH) | 99% |
| methyl oleate | 9, 1000 / THF, 14 h | C8H17-CH=CH-(CH2)8-OH | 8% |
|  |  | C8H17-CH=CH-(CH2)8-OH (isomer) | 32% |
|  |  | C8H17-(CH2)9-OH (octadecan-1-ol) | 60% |
| triolein (triglyceride of oleic acid) | 2, 2000 / Toluene, 6.5 h | (Z)-octadec-9-en-1-ol (C8H17-CH=CH-(CH2)8-OH) | 98% |
| Extra-virgin olive oil[b] | 2, 1000 / Toluene, 6.5 h | C6H17-(CH2)n-OH and C8H17-CH=CH-(CH2)8-OH | ca. 90% |
|  | 2, 3000 / Toluene, 19 h |  | (ca. 85%) |

[a] with tBuOK., 0.5 mol %.

[b] A mixture of triglycerides of oleic (ca. 5%), linoleic (ca. 2-3%), and palmitic acids as the main components in our samples.

Example 8—Hydrogenation of Methyl Benzoate Using Complex 2

1 mL of a solution containing 4.7 mg/mL of 2 (0.01 mmol [Os]) in THF or toluene was added to a solution of methyl benzoate (2.72 g, 20.0 mmol) in 6 mL of THF or toluene. The subsequent manipulations were carried out following the procedure in Example 7.

Example 9—Hydrogenation of Olive Oil Using Complex 2

0.6 mL of a 4.7 mg/mL solution of 2 in toluene (containing 0.006 mmol [Os]) was added to a solution of olive oil (1.86 g, 2.00 mmol) in 6 mL of toluene. All subsequent manipulations were carried out following the procedure in Example 7 using a 7 h reaction time. The product mixture was evaporated and dried under vacuum for 1 h. Further separation of the fatty alcohol from glycerol could be performed by hexane extraction or by centrifugation and decantation of the fatty alcohol from glycerol.

Example 10—Hydrogenation of Methyl Caproate Using Complex 3

1 mL of a 4.2 mg/mL solution of 3 (0.01 mmol) in THF or toluene and tBuOK (22.6 mg, 0.2 mmol) were added to a solution of methyl caproate (2.94 g, 20.0 mmol) in 6 mL of THF or toluene. All subsequent manipulations were carried out following the procedure described in Example 7.

Example 11—Synthesis of $NH_2(CH_2)_2PPH_2$

In a 500 mL flask, 50.0 g (0.191 mol) of $PPh_3$ was dissolved in 200 mL of THF and 4.00 g (0.571 mol) of granulated Li was added. The mixture rapidly changed color to bright-orange, then to dark-red. The reaction was stirred overnight, and then the product solution was filtered through a glass frit into a 500 mL flask. Slow addition of 19.3 g (0.166 mol) of 2-chloroethylamine hydrochloride to the filtrate (Caution: Exothermic reaction!) afforded a light-orange solution that was left to stir for an additional 30 min and then was treated with 3.00 g of $H_2O$. Solvent removal under vacuum afforded a viscous residue. The crude product was washed with 3×20 mL of hexane and the remaining white slurry was extracted with 70 mL of toluene and filtered through a short plug (2 cm×1 cm) of $Al_2O_3$. The toluene extract was evaporated using a rotavap and subsequently dried under vacuum to give 34.69 g (91%) of crude (83-85%) $NH_2(CH_2)_2PPh_2$ as a light-yellow oil. This product was used without purification in the synthesis of Example 12.

Example 12—Synthesis of PyCH=NCH$_2$CH$_2$PPh$_2$

A solution of 2-picolyl aldehyde (23.2 g, 0.216 mol) in 20 mL of THF was slowly added to 60 g (83%, 0.218 mol) of 2-aminoethyl diphenylphosphine in 80 mL of THF and the mixture was stirred for 3 h. Then, 40 mL of hexane was added and the mixture was left in a refrigerator at −18° C., which produced an off-white precipitate. The solid was filtered off, washed with denatured ethanol (2×10 mL) and 40 mL of hexane, and then dried under vacuum for 2 h. The product was obtained as an off-white solid. Yield 47.2 g (68%).

$^1$H NMR ([D6]Benzene) δ=8.54-8.33 (m, 2H, Py+NCH), 8.09 (dd, J=7.9, 1.0 Hz, 1H, Py), 7.54-7.32 (m, 4H, Ph), 7.12-6.99 (m, 7H, Ph+Py), 6.71-6.53 (m, 1H, Py), 3.79-3.55 (m, 2H, CH$_2$), 2.46-2.24 (m, 2H, CH$_2$). $^{13}$C NMR ([D6] Benzene) δ=162.70 (s, 1C, Py), 155.78 (s, 1C, N=C), 149.64 (s, 1C, Py), 139.56 (d, J(CP)=14.3 Hz, 2C, {ArP}C$^{ipso}$), 136.05 (s, 1C, Py), 133.30 (d, J(CP)=19.0 Hz, 4C, {ArP}C$^{ortho}$), 128.87 (s, 2C, {Ar}C$^{para}$), 128.78 (s, 4C, {Ar}C$^{meta}$), 124.53 (s, 1C, Py), 121.04 (s, 1C, Py), 58.45 (d, J(CP)=20.3 Hz, 1C, NCH$_2$), 30.50 (d, J(CP)=13.9 Hz, 1C, CH$_2$P). $^{31}$P NMR ([D6]Benzene) δ=−18.19 (s).

Example 13—Synthesis of PyCH$_2$NH(CH$_2$)$_2$PPh$_2$ 40 g (0.126 mol) of PyCH=NCH$_2$CH$_2$PPh$_2$ was suspended in 100 mL of methanol in a 250 mL flask, followed by slow addition of 5.24 g (0.138 mol) of NaBH$_4$ over a 2 h period of time. After further stirring for 30 min, the mixture was evaporated and the oily residue was extracted with 3×30 mL of toluene. The toluene solution was filtered through a short plug of Al$_2$O$_3$ (2 cm×2 cm), using additional 2×20 mL of toluene to wash the solids. The solvent was removed under vacuum and the product was dried for an additional 2 h to yield 37.2 g (92%) of a pale-yellow oil that crystallized upon further standing (after 7-10 days) at room temperature.

$^1$H NMR ([D6]Benzene) δ=8.46 (ddd, J=4.8, 1.7, 1.0 Hz, 1H, Py), 7.53-7.31 (m, 4H, Ph), 7.12-6.91 (m, 6H, Ph), 6.62 (ddd, J=7.2, 4.8, 1.5 Hz, 1H, Py), 3.79 (s, 2H, CH$_2$), 2.75 (dd, J=15.2, 8.5 Hz, 2H, CH$_2$), 2.25-2.02 (m, 2H, CH$_2$), 1.67 (br. s, 1H, NH). $^{13}$C {$^1$H} NMR ([D6]Benzene) δ=161.06 (s, 1C, Py), 149.48 (s, 1C, Py), 139.74 (d, J(CP)=14.2 Hz, 2C, {ArP}C$^{ipso}$), 135.84 (s, 1C, Py), 133.18 (d, J(CP)=18.8 Hz, 4C, {ArP}C$^{ortho}$), 128.69 (d, J(CP)=6.5 Hz, 4C, {ArP}C$^{meta}$), 128.62 (s, 2C, {ArP}C$^{para}$), 121.94 (s, 1C, Py), 121.61 (s, 1C, Py), 55.39 (s, 1C, CH$_2$N), 46.79 (d, J(CP)=20.7 Hz, 1C, NCH$_2$), 29.79 (d, J(CP)=12.9 Hz, 1C, CH$_2$P).

Example 14—Synthesis of trans-OsHCl(CO) [PyCH$_2$NH(CH$_2$)$_2$PPh$_2$]

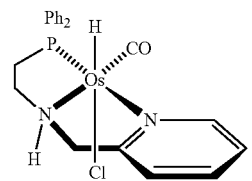

Complex 4

A flask containing a mixture of OsHCl(CO)(AsPh$_3$)$_3$ (3.00 g, 2.56 mmol) and PyCH$_2$NH(CH$_2$)$_2$PPh$_2$ (0.818 g, 2.56 mmol) in 30 mL of diglyme was placed in an oil bath preheated to 160° C., and stirred for 3 h affording a dark-red solution. After cooling to room temperature, the mixture was diluted with 30 mL of hexane, and the flask was stored for 1 h in a freezer at −23° C. The precipitated product was filtered off, washed with diethyl ether (3×5 mL), and recrystallized from 20 mL DCM:Et$_2$O mixture (3:1). Yield: 779 mg (53%).

$^1$H {$^{31}$P} NMR ([D2]DCM) δ=9.04 (d, J=5.1 Hz, 1H, Py), 7.81-7.59 (m, 5H, Ph+Py), 7.45-7.30 (m, 6H, Ph), 7.28-7.16 (m, 2H, Py), 4.64 (dd, J=14.6, 4.4 Hz, 1H, CH$_2$), 4.50 (br t, J=−11.5 Hz, 1H, NH), 3.96 (dd, J=14.1, 11.7 Hz, 1H, CH$_2$), 3.80-3.67 (m, 1H, CH$_2$), 3.09 (dd, J=14.5, 1.9 Hz, 1H, CH$_2$), 2.74 (dtd, J=14.7, 11.6, 3.3 Hz, 1H, CH$_2$), 2.32 (td, J=14.6, 5.4 Hz, 1H. CH$_2$), −15.81 (s, 1H, OsH). $^{13}$C {$^1$H} NMR ([D2]DCM) δ=188.19 (dd, J(CP)=9.2, 5.6 Hz, residual coupling with OsH, 1C, CO), 161.63 (s, 1C, Py), 154.20 (d, J(CP)=1.5 Hz, 1C, Py), 139.78 (d, J(CP)=54.6 Hz, 1C, {Ar}C$^{ipso}$), 136.70 (s, 1C, Py), 135.90 (d, J(CP)=50.4 Hz, 1C, {Ar}C$^{ipso}$), 133.61 (d, J(CP)=10.9 Hz, 1C, 2C, {Ar}C$^{ortho}$), 132.69 (d, J(CP)=10.8 Hz, 2C, {Ar}C$^{ortho}$), 130.50 (d, J(CP) 2.4 Hz, 1C, {Ar}C$^{para}$), 130.36 (d, J(CP)=2.4 Hz, 2C, {Ar}C$^{para}$), 128.82 (d, J(CP)=10.4 Hz, 2C, {Ar}C$^{meta}$), 128.66 (d, J(CP)=10.4 Hz, {Ar}C$^{meta}$), 125.34 (d, J(CP)=2.0 Hz, Py), 122.02 (d, J(CP)=1.5 Hz, Py), 60.63 (s, 1C, PyCH$_2$), 53.73 (d, J(CP)=2.1 Hz, 1C, NCH$_2$), 35.91 (d, J(CP)=30.8 Hz, 1C, CH$_2$P). $^{31}$P {$^1$H} NMR ([D2]DCM) δ=29.7 (s).

Example 15—Synthesis of trans-RuHCl(CO) [PyCH$_2$NH(CH$_2$)$_2$PPh$_2$]

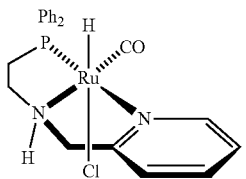

Complex 5

A 50 mL Schlenk flask containing a mixture of RuHCl (CO)(AsPh$_3$)$_3$ (5.73 g, 4.68 mmol) and PyCH$_2$NH(CH$_2$)$_2$PPh$_2$ (1.5 g, 4.68 mmol) in 30 mL of dioxane was stirred under reflux for 3 h affording a dark brown solution. After cooling to room temperature, the mixture was diluted with 5 mL of Et$_2$O and left in a refrigerator at −15° C. The crystallized product was filtered, then washed with diethyl ether (2×5 mL), and dried under vacuum. Yield: 1.71 g (75%) of a grey solid.

$^1$H {$^{31}$P} NMR ([D2]DCM) δ=8.97 (d, J=5.4 Hz, 1H, Py), 7.95-7.55 (m, 5H, Ph+Py), 7.47-7.35 (m, 6H, Ph), 7.33-7.26 (m, 1H, Py), 7.22 (d, J=7.8 Hz, 1H, Py), 4.45 (dd, J=15.3, 4.2 Hz, 2H, PyCH$_2$), 4.09 (dd, J=15.3, 12.7 Hz, 1H, CH$_2$), 3.71-3.51 (br, 1H, NH), 3.00 (dd, J=14.1, 1.8 Hz, 1H, CH$_2$), 2.75 (dtd, J=−14.3, 11.3, 3.1 Hz, 1H, CH$_2$), 2.53 (td, J=14.4, 5.1 Hz, 1H, CH$_2$), −14.30 (s, 1H, RuH). $^{13}$C {$^1$H} NMR ([D2]DCM) δ=205.80 (d, J(CP)=17.9 Hz), 160.84 (s, 1C, Py), 153.92 (d, J(CP)=1.1 Hz, 1C, Py), 138.73 (d, J(CP)=49.5 Hz, 1C, {Ar}C$^{ipso}$), 137.14 (s, 1C, Py), 135.66 (d, J(CP)=43.7 Hz, 1C, {Ar}C$^{ipso}$), 133.46 (d, J(CP)=11.0 Hz, 2C, {Ar}C$^{ortho}$), 132.62 (d, J(CP)=11.4 Hz, 2C, {Ar}C$^{ortho}$), 130.44 (d, J(CP)=2.4 Hz, 1C, {Ar}C$^{para}$), 130.34 (d, J(CP)=2.3 Hz, 1C, {Ar}C$^{para}$), 128.84 (d, J(CP)=10.1 Hz, 2C, {Ar}C$^{meta}$), 128.61 (d, J(CP)=10.1 Hz, 2C, {Ar}C$^{meta}$), 124.61 (d, J(CP)=2.2 Hz, 1C, Py), 121.75 (d, J(CP)=1.6 Hz, 1C, Py), 59.77 (d, J(CP)=1.5 Hz, 1C, CH$_2$), 51.92 (d, J(CP)=4.1 Hz, 1C, CH$_2$), 35.14 (d, J/(CP)=26.0 Hz, 1C, CH$_2$). Anal. Calcd for C$_{20}$H$_{21}$ClN$_2$ORuP: C, 47.23; H, 6.61; N, 7.34. Found: C, 46.95; H, 6.53; N, 7.15.

Example 16—Typical Procedure for Acceptorless Alcohol Dehydrogenation

A 50 mL Schlenk flask equipped with a stir bar was charged with 0.052 mmol of Complex 2, 3, or 5, 0.5-1 mol % of tBuOK (with 3 and 5), and the calculated amount of substrate (1000:1, substrate to metal ratio) under argon. Then, the flask (attached to and vented through an argon manifold) was placed in an oil bath, where it was heated at a temperature slightly exceeding the boiling point of the neat alcohol. The conversion was monitored by 1H NMR spectroscopy using 0.6 mL samples retrieved from the reaction solutions through the septum stopper with the help of a syringe.

TABLE 5

Results of catalytic acceptorless dehydrogenation of alcohols.

| Entry | R[a] | T, ° C. | cat | ROH/[M][b] | t, h | Conversion, % |
|---|---|---|---|---|---|---|
| 1 | Me | 78 | 5[e] | 1000 | 7.5 | 9 |
| 2 | Me | 78 | 5[c, e] | 1000 | 19 | 25 |
| 3 | Me | 78 | 2 | 1000 | 24 | 7 |
| 4 | Me | 78 | 2[e] | 1000 | 8 | 61 |
| 5 | Me | 78 | 2[c, d] | 1000 | 8 | 96 |
| 6 | Me | 78 | 3[d] | 1000 | 7.5 | 30 |
| 7 | Me | 78 | 7[f] | 2000 | 16 | 95 |
| 8 | Me | 78 | 7[g] | 10000 | 24 | 91 |
| 9 | Me | 78 | 7[g] | 20000 | 40 | 85 |
| 10 | Me | 78 | 7[f][h] | 2000 | 16 | 89 |
| 11 | Et | 96 | 5[e] | 1000 | 6 | 69 |
| 12 | Et | 96 | 2 | 1000 | 8.5 | 86 |
| 13 | Et | 96 | 3[d] | 1000 | 8 | 73 |
| 14 | Pr | 118 | 5[e] | 1000 | 2 | 73 |
| 15 | Pr | 118 | 2 | 1000 | 3 | 93 |
| 16 | Pr | 118 | 3[d] | 1000 | 3 | 78 |
| 17 | i-Amyl | 131 | 5[e] | 1000 | 2.5 | 88 |
| 18 | i-Amyl | 131 | 2 | 1000 | 3 | 86 |
| 19 | i-Amyl | 131 | 3[d] | 1000 | 2.5 | 92 |
| 20 | Hexyl | 158 | 5[e] | 1000 | 2 | 86 |
| 21 | Hexyl | 158 | 2 | 1000 | 1.3 | 97 |
| 22 | Hexyl | 158 | 2 | 4000 | 1.3 | 71 |
| 23 | Hexyl | 158 | 3[d] | 1000 | 1 | 86 |

[a]Using 52 mmol of neat substrate and 1 mol % of EtONa for catalyst 7.
[b]Substrate to metal molar ratio.
[c]In toluene.
[d]With 0.5 mol % of tBuOK.
[e]With 1 mol % of iBuOK.
[f]Using 0.1 mol of neat substrate.
[g]Using 0.2 mol of neat substrate.
[h]Reaction was prepared in air using standard anhydrous grade ethanol Example 17—Synthesis of PyCH$_2$NH(CH$_2$)$_2$PtBu$_2$ The synthesis of NH$_2$(CH$_2$)$_2$PtBu$_2$ was performed following a known procedure (6, incorporated herein by reference). A solution of 2-picolyl aldehyde (2.04 g, 19.04 mmol) in 10 mL of THF was added to 2-(di-tert-butylphosphino)ethylamine (3.60 g, 19.04 mmol) in 10 mL of THF. The mixture was stirred for 1 h, then evaporated and dried for 1 h under vacuum. The oily residue was re-dissolved in 15 mL of toluene and was slowly (over a period of 1 h) treated with 1.5M solution of DIBAL in toluene (16.5 mL, 24.75 mmol) (Caution: exothermic reaction!). The product solution was stirred for 30 min, and then quenched with 1 mL of water (Caution: exothermic reaction!). The resulting suspension was filtered through a short plug (2.1 cm) of basic alumina and the solids were washed with THF (3×10 mL). The filtrate was evaporated and dried under vacuum for 3 h to give the product as a yellow oil (3.79 g, 71%).

$^1$H {$^{31}$P} NMR ([D6]Benzene) δ=8.49 (d, J=4.8 Hz, 1H, Py), 7.19-7.15 (m, 1H, Py overlapped with C$_6$D$_5$H) 7.10 (t, J=7.1 Hz, 1H, Py), 6.64 (dd, J=6.3, 5.8 Hz, 1H, Py), 3.96 (s, 2H, PyCH$_2$), 2.87 (t, J=7.7 Hz, 2H, NCH$_2$), 1.91 (br, 1H, NH) 1.56 (t, J=7.7 Hz, 2H, CH$_2$P), 1.07 (s, 18H, CH$_3$). $^{13}$C {$^1$H} NMR ([D6]Benzene) δ=161.46 (s, 1C, Py), 149.48 (s, 1C, Py), 135.84 (s, 1C, Py), 121.91 (s, 1C, Py), 121.58 (s, 1C, Py), 55.79 (s, 1C, CH$_2$), 50.78 (d, J(CP)=34.2 Hz, 1C, CH$_2$), 31.19 (d, J(CP)=22.1 Hz, 2C, CMe$_3$), 29.82 (d, J(CP)=14.0 Hz, 6C, CH₃), 22.96 (d, J(CP)=27.5 Hz, 1C, CH₂P). ³¹P {¹H} NMR ([D6]Benzene) δ=20.47 (s).

Example 18—Synthesis of trans-RuHCl(CO)[PyCH₂NH(CH₂)₂PtBu₂]

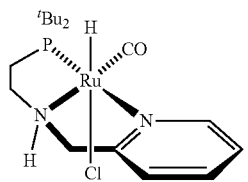

Complex 6

A mixture of RuHCl(CO)(AsPh₃)₃ (1.93 g, 1.79 mmol) and PyCH₂NH(CH₂)₂PtBu₂ (500 mg, 1.79 mmol) in 10 mL of diglyme was stirred for 3 h at 140° C. in a 50 mL Schlenk flask. After cooling to room temperature, 2 mL of Et₂O was added, and the mixture was left to crystallize at −18° C. The product was filtered, washed with diethyl ether (2×3 mL), and dried under vacuum to give a grey solid. Yield: 431 mg (54%).

¹H {³¹P} NMR ([D2]DCM) δ=8.89 (dt, J=5.4, 0.8 Hz, 1H; Py), 7.66 (td, J=7.7, 1.6 Hz, 1H; Py), 7.22 (dd, J=15.5, 7.2 Hz, 2H; Py), 4.68 (br., 1H; NH), 4.45 (dd, J=15.0, 4.7 Hz, 1H; CH₂), 4.00 (dd, J=14.9, 11.5 Hz, 1H; CH₂), 3.61-3.44 (m, 1H; CH₂), 2.67 (dtd, J=13.4, 11.6, 4.8 Hz, 1H; CH₂), 2.26 (dd, J=14.7, 4.2 Hz, 1H; CH₂), 2.07 (td, J=14.2, 6.4 Hz, 1H; CH₂), 1.35 (d, J=5.3 Hz, 18H; CH₃), −15.59 (s, 1H; RuH), ¹³C {¹H} NMR ([D2]DCM) δ 206.49 (dd, J(CP)=15.5, J(CH)=6.9 Hz residual coupling with OsH, 1C; CO), 160.73 (s, 1C; Py), 153.59 (s, 1C; Py), 136.74 (s, 1C; Py), 124.37 (d, J(CP)=1.6 Hz, 1C; Py), 121.33 (s, 1C; Py), 52.51 (s, 1C; CH₂), 38.29 (d, J(CP)=15.0 Hz, 1C; CH₂), 37.55 (d, J(CP)=24.6 Hz, 1C; CMe₃), 37.52 (d, J(CP)=24.6 Hz, 1C; CMe₃), 30.93 (d, J(CP)=4.3 Hz, 3C; CH₃), 30.07 (d, J(CP)=3.2 Hz, 3C; CH₃), 28.49 (d, J(CP)=14.9 Hz, 1C; PCH₂). ³¹P {¹H} NMR ([D2]DCM) δ 106.10 (s). Anal. Calcd for C₁₇H₃₁ClN₂OPRu: C, 45.68; H, 6.99; N, 6.27. Found: C, 45.40; H, 6.74; N, 5.92.

Example 19—Synthesis of trans-RuCl₂(PPh)[PyCH₂NH(CH₂)₂PPh₂]

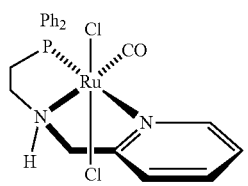

Complex 7

Stirring a mixture of RuCl₂(PPh)₃ (4.20 g, 4.38 mmol) and PyCH₂NH(CH₂)₂PPh₂ (1.40 g, 4.38 mmol) in 30 mL of toluene (or 1,4-dioxane) for 3 h at 40° C. in a 100 mL Schlenk flask produced a yellow suspension. The product was filtered in air, washed with 10 mL of Et₂O, and dried under vacuum for 2 h to give a yellow solid. Yield: 3.1 g (94%).

¹H {³¹P} NMR ([D2]DCM) δ 8.42 (d, J=5.6 Hz, 1H; Py), 7.77-7.53 (m, 3H), 7.53-6.91 (m, 29H), 6.85 (t, J=6.6 Hz, 1H; Py), 5.49 (t, J=13.0 Hz, 1H; CH₂), 5.23 (br, 1H; NH), 4.28 (dd, J=13.9, 3.5 Hz, 1H; CH₂), 3.66-3.31 (m, 2H; CH₂), 2.91-2.57 (m, 2H; CH₂), 2.35 (s, 3H; CH₃Tol), ¹³C {¹H} NMR ([D2]DCM) δ 163.50 (s, 1C; Py), 156.81 (s, 1C; Py), 139.44 (d, J=32.2 Hz, 2C; {PPh₂}C$^{ipso}$), 137.89 (s, 1C; Py), 137.13 (d, J(CP)=39.3, 3C; {PPh₃}C$^{ipso}$), 135.95-135.29 (m, 6C; {PPh₃}C$^{ortho}$), 135.11 (d, J(CP)=8.4 Hz, 2C; {PPh₂}C$^{ortho}$), 134.47 (d, J(CP)=9.1 Hz, 2C; {PPh₂}C$^{ortho}$), 129.38 (d, J(CP)=4.5 Hz, 2C; {PPh₂}C$^{para}$), 129.38 (s, 3C; {PPh₃}C$^{para}$), 128.48-127.05 (m, 10C; {PPh₂}C$^{meta}$+{PPh₃}C$^{meta}$), 122.96 (s, 1C; Py), 121.92 (s, 1C; Py), 67.59 (s, 1,4-dioxane), 57.77 (s, 1C; CH₂), 49.09 (s, 1C; CH₂), 38.77 (d, J(CP)=27.4 Hz, 1C; CH₂). ³¹P {¹H} NMR ([D2]DCM) δ 49.13 (d, J(PP)=28.9 Hz, 1P), 47.39 (d, J(PP)=29.0 Hz, 1P). Anal. Calcd for C₃₈H₃₆Cl₂N₂P₂Ru.C₇H₈: C, 63.83; H, 5.24; N, 3.31. Found: C, 63.23; H, 5.22; N, 3.34.

Example 20—Synthesis of trans-OsHCl(CO)[PyCH₂NH(CH₂)₂PtBu₂]

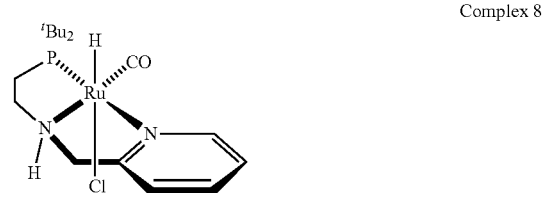

Complex 8

A mixture of OsHCl(CO)AsPh₃)₃ (1.675 g, 1.43 mmol) and PyCH₂NH(CH₂)₂PtBu₂ (400 mg, 1.43 mmol) in 10 mL of diglyme was stirred for 3 h at 140° C. in a 50 mL Schlenk flask. After cooling to room temperature, 2 mL of Et₂O was added, and the product crystallized upon standing at −15° C. The yellow solid was filtered, washed with diethyl ether (2×3 mL) and dried under vacuum. Yield: 507 mg (66%).

¹H {³¹P} NMR ([D2]DCM) δ 8.97 (dt, J=6.3, 1.4 Hz, 1H; Py), 7.67 (td, J=7.8, 1.5 Hz, 1H; Py), 7.27-7.05 (m, 2H; Py), 4.65 (dd overlapping with br. s, J=15.8, 4.7 Hz, 2H; CH₂+NH), 3.88 (dd, J=15.8, 12.2 Hz, 1H; CH₂), 3.69-3.43 (m, 1H; CH₂), 2.64 (ddd, J=25.1, 11.4, 4.6 Hz, 1H; CH₂), 2.33 (dt, J=29.2, 14.5 Hz, 1H; CH₂), 1.99 (td, J=14.4, 6.4 Hz, 1H; CH₂), 1.35 (s, 18H; CH₃), −17.35 (s, 1H; OsH), ¹³C {¹H} NMR ([D2]DCM) δ 188.49 (dd, J(CP)=8.3, J(CH)=4.3 Hz residual coupling with OsH, 1C; CO), 161.44 (s, 1C; Py), 153.79 (d, J(CP)=1.7 Hz, 1C; Py), 136.22 (s, 1C; Py), 125.08 (d, J(CP)=1.8 Hz, 1C; Py), 121.55 (d, J(CP)=1.6 Hz, 1C; Py), 54.22 (s, 1C; CH₂), 39.63 (d, J(CP)=20.8 Hz, 1C; CH₂), 38.96 (d, J(CP)=29.1 Hz, 2C; CMe), 30.90 (d, J(CP)=3.9 Hz, 3C; CH₃), 29.78 (d, J(CP)=2.6 Hz, 3C; CH₃), 29.22 (d, J(CP)=19.8 Hz, 1C; CH₂). ³¹P {¹H} NMR ([D2]DCM) δ 62.79 (s). Anal. Calcd for C₁₇H₃₁ClN₂OPOs: C, 38.16; H, 5.65; N, 5.24. Found: C, 38.04; H, 5.72; N, 4.97.

Example 21—Imine and Ester Hydrogenation Using Complex 7

Complex 7 was further tested in hydrogenation of compounds with polar C=X bonds. There has been much recent interest in the catalytic hydrogenation of esters. Although the performance of the "state of the art" industrial catalysts is impressive, further improvements are highly desirable to (a) reduce the reaction temperature, preferably to as low as 20-40° C., and (b) reduce the catalyst loading, preferably to less than 0.05 mol %. Guided by these considerations, complex 7 was tested in the hydrogenation of several benchmark substrates, shown in tables 1-4, above. Note that all of the reactions shown were performed at 40° C.

In an argon glovebox, the required amount of a 1.9 mg/g solution of 4 in THF was added to the desired amount of base (tBuOK, MeOK, or EtOK). The obtained mixture was then mixed with the substrate (0.02-0.20 mol) and transferred into a stainless-steel Parr reactor (75 mL or 300 mL) equipped with a magnetic stir bar. The reactor was closed, taken out of the glovebox, tightened and connected to a hydrogen tank. After purging the line, the reactor was pressurized to 725 psi (50 Bar) and disconnected from the $H_2$ source (with the exception of reactions conducted in the 300 mL reactor using 0.2 mol of substrate). Then, the reactor was placed in an oil bath preheated to 40° C. At the end of the reaction time, the reactor was moved into a cold water bath for 5 min and depressurized.

The results of the above hydrogenation experiments demonstrate that an outstanding ethanol dehydrogenation catalyst might also have superior efficiency in hydrogenation of substrates with polar C=X bonds. Catalyst 7 is particularly successful for the reduction of alkanoates, giving an unprecedented 20 000 turnovers in 16 h for ethyl acetate and 18 800 turnovers in 18 h for methyl hexanoate, both at 40° C. The best turnover number (TON) reported to date for this type of substrate was 7100 in 18 h at 100° C. for methyl hexanoate, using a ruthenium dimer $\{RuH(CO)[N(C_2H_4PiPr_2)_2]\}_2$ (Spasyuk, D., Smith, S., Gusev, D. G. Angew. Chem., Int. Ed. 2012, 51, 2772-2775). For another comparison, the best Firmenich catalyst, $RuCl_2(H_2NC_2H_4PPh_2)_2$, would theoretically need 27 h to produce 18 600 turnovers for methyl octanoate at 100° C., on the basis of the reported TOF=688 $h^{-1}$ over a 2.5 h reaction time. (United States patent application publication No. US 2010-280273). Complex 7 is also a competent imine hydrogenation catalyst, giving a particularly high TON=50 000 for N-benzylaniline.

Example 22—Synthesis of $\mu_N$-(RuH(CO)[PyCH$_2$N(CH$_2$)$_2$P(iPrh)$_2$]$_2$

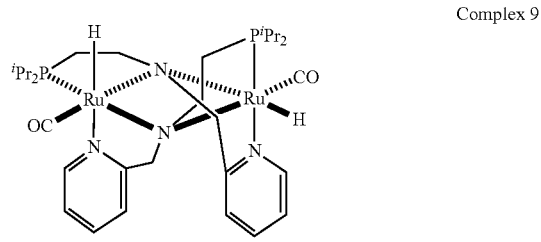

Complex 9

A mixture of diethyl ether and THF (2:1, 15 mL) was added to a mixture of Complex 3 (640 mg, 1.53 mmol) and tBuOK (172 mg, 1.53 mmol) and the resulting solution was stirred for 5 min. During this time the color changed from yellow to dark purple, then to dark green. The product solution was placed into a freezer at −18 degrees Celsius for 15 min and subsequently filtered through a glass frit. The solvent was removed under vacuum to yield 532 mg (91%) of a mixture of two isomers of Complex 4. The major isomer was obtained in a pure form as a bright yellow solid (340 mg, 58%) after recrystallization of the mixture from 5 mL of toluene at 60° C.

$^{31}$P {$^1$H} NMR ([D2]DCM) δ=93.80 (s), 90.25 (s). $^1$H {$^{31}$P} NMR ([D2]DCM) δ=9.01 (dd, J=5.5, 0.8 Hz, 1H; Py), 8.40 (d, J=5.4 Hz, 1H; Py), 7.15 (td, J=7.7, 1.6 Hz, 1H; Py), 7.10 (td, J=7.7, 1.7 Hz, 1H; Py), 6.86 (t, J=6.5 Hz, 2H; Py), 6.46 (d, J=7.9 Hz, 1H; Py), 6.27 (d, J=8.0 Hz, 1H; Py), 4.50 (d, J=18.0 Hz, 1H; CH$_2$), 4.15 (d, J=17.9 Hz, 1H; CH$_2$), 4.05 (dd, J=18.0, 1.6 Hz, 1H, CH$_2$), 3.55-3.24 (m, 3H), 3.11 (dd, J=11.8, 5.3 Hz, 1H; CH$_2$), 2.95-2.78 (m, 2H), 2.61-2.45 (m, 1H), 2.37-2.17 (m, 2H), 2.03 (dd, J=−13.4, 3.8 Hz, 1H; CH$_2$), 1.91 (hept, J=7.2 Hz, 1H; CH), 1.74 (td, J=14.1, 5.6 Hz, 1H; CH$_2$), 1.53-1.43 (dd overlapped with d, 1H; CH$_2$), 1.44 (d overlapped with dd, J=7.6 Hz, 3H; CH$_3$), 1.38 (d, J=2.4 Hz, 3H; CH$_3$), 1.35 (d, J=1.8 Hz, 3H; CH$_3$), 1.31 (d, J=6.9 Hz, 3H; CH$_3$), 1.16 (d, J=6.8 Hz, 3H; CH$_3$), 1.05 (d, J=6.9 Hz, 6H; CH$_3$), 1.00 (d, J=6.8 Hz, 3H; CH$_3$), −12.45 (s, 1H; RuH), −13.68 (s, 1H; RuH). $^{13}$C {$^1$H} NMR ([D6]Benzene) δ=209.64 (d. J(CP)=17.0 Hz, 1C; CO), 207.30 (d, J(CP)=12.4 Hz, 1C; CO), 169.03 (d, J(CP)=2.2 Hz, 1C; Py), 168.09 (s, 1C; Py), 155.64 (s, 1C; Py), 151.26 (s, 1C; Py), 134.92 (s, 1C; Py), 134.51 (s, 1C; Py), 121.37 (d, J(CP)=2.4 Hz, 1C; Py), 120.97 (s, 1C; Py), 118.09 (s, 1C; Py), 117.65 (s, 1C; Py), 74.01 (d, J(CP)=2.6 Hz, 1C; PyCH$_2$), 71.36 (m, 2C; PyCH$_2$+NCH$_2$), 69.73 (s, 1C; NCH$_2$), 33.66 (d, J(CP)=22.8 Hz, 1C; CH), 31.68 (d, J(CP)=11.5 Hz, 1C; CH), 29.39 (d, J(CP)=4.1 Hz, 1C; CH$_2$), 29.11 (s, 1C; CH$_2$), 26.64 (d, J(CP)=29.2 Hz, 1C; CH), 25.11 (d, J(CP)=32.6 Hz, 1C, CH), 21.60 (d, J(CP)=4.1 Hz, 1C; CH$_3$), 21.47 (d, J(CP)=5.1 Hz, 1C; CH$_3$), 21.07 (d, J(CP)=7.3 Hz, 1C; CH$_3$), 20.94 (d, J(CP)=5.0 Hz, 1C; CH$_3$), 19.77 (s, 1C; CH$_3$), 19.41 (s, 1C; CH$_3$), 17.69 (d, J(CP)=3.2 Hz, 1C; CH$_3$), 17.59 (d, J(CP)=2.9 Hz, 1C; CH$_3$). Anal. Calcd for $(C_{15}H_{25}N_2RuOP)_2$: C, 47.23; H, 6.61; N, 7.34. Found: C, 46.95; H, 6.53; N, 7.15.

Example 23—Crystal Structure Determination of Complex 7

Single crystals of complex 7 were grown by slow diffusion of hexanes into a saturated solution in dichloromethane. The data was collected on a Bruker Microstar™ generator equipped with Helios optics, a Kappa Nonius™ goniometer, and a Platinum-135 detector. Cell refinement and data reduction were done using SAINT™ (SAINT (1999) Release 6.06; Integration Software for Single Crystal Data. Bruker AXS Inc., Madison, Wis., USA.) An empirical absorption correction, based on the multiple measurements of equivalent reflections, was applied using the program SADABS™ (Sheldrick, G. M. (1999). SADABS, Bruker Area Detector Absorption Corrections. Bruker AXS Inc., Madison, Wis., USA.). The space group was confirmed by XPREP routine of SHELXTL (XPREP (1997) Release 5.10; X-ray data Preparation and Reciprocal space Exploration Program, Bruker AXS Inc., Madison, Wis., USA.; SHELXTL (1997) Release 5.10; The Complete Software Package for Single Crystal Structure Determination, Bruker AXS Inc., Madison, Wis., USA.). The structure was solved by direct-methods and refined by full-matrix least squares and difference Fourier techniques with SHELX-97 as a part of LinXTL tool box (Sheldrick, G. M. (1997). SHELXS97, Program for the Solution of Crystal Structures. Univ. Of Gottingen, Germany; Sheldrick, G. M. (1997). SHELXL97, Program for the Refinement of Crystal Structures. University of Gottingen, Germany.). All non-hydrogen atoms were refined with anisotropic displacement parameters. Hydrogen atoms were set in calculated positions and refined as riding atoms with a common thermal parameter, except those of the NH moiety and hydrides, which were positioned from residual peaks in the difference Fourier map. The collection parameters and bond distances and angles can be found in tables 5 and 6, respectively.

TABLE 6

Crystal Data Collection and Refinement Parameters for Complex 7

| | |
|---|---|
| chemical formula | $C_{38}H_{36}Cl_2N_2P_2Ru$ |
| crystal colour | Yellow |
| Fw; F(000) | 754.60; 772 |
| T (K) | 150 |
| wavelength (Å) | 1.54178 |
| space group | P-1 |
| a (Å) | 10.5195(3) |
| b (Å) | 13.2513(3) |
| c (Å) | 16.3644(4) |
| α(deg) | 68.972(1) |
| β(deg) | 88.622(1) |
| γ(deg) | 67.031(1) |
| Z | 2.00 |
| V (Å³) | 1942.49(9) |
| $\rho_{calcd}$ (g · cm⁻³) | 1.290 |
| μ (mm⁻¹) | 5.511 |
| θ range (deg); completeness | 4.61-69.76; 0.971 |
| collected reflections; $R_\sigma$ | 30435; 0.0328 |
| unique reflections; $R_{int}$ | 30435; 0.0386 |
| $R1^a$; $wR2^b$ [I > 2σ(I)] | 0.0297; 0.0765 |
| R1; wR2 [all data] | 0.0299; 0.0767 |
| GOF | 0.975 |
| largest diff peak and hole | 1.054 and −0.464 |

TABLE 7

Selected Bond Distances (Å) and Angles (deg) for Complex 7

| | |
|---|---|
| Ru1—N1 | 2.143(2) |
| Ru1—N2 | 2.160(2) |
| Ru1—P1 | 2.302(5) |
| Ru1—P2 | 2.3305(4) |
| Ru1—Cl2 | 2.4093(4) |
| Ru1—Cl1 | 2.4138(4) |
| N1—Ru1—N2 | 75.46(6) |
| N1—Ru1—P1 | 83.43(5) |
| N2—Ru1—P1 | 158.00(4) |
| N2—Ru1—P2 | 97.93(4) |
| P1—Ru1—P2 | 103.56(2) |
| P1—Ru1—Cl2 | 95.6(2) |

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A complex of Formula II or III

[M(LNN')$Z_a$]     (II)

$\mu^N$[M(LNN')$Z_a$]$_2$     (III)

wherein:

each Z is independently a hydrogen or halogen atom, a $C_1$-$C_6$ alkyl, a hydroxyl, or a $C_1$-$C_6$ alkoxy, a nitrosyl (NO) group, CO, PMe$_3$, PPh$_3$, or CNR, wherein R is an alkyl or an aryl;

M is Ru or Os;

a is 2 or 3;

each LNN' is a coordinated ligand that is a compound according to:

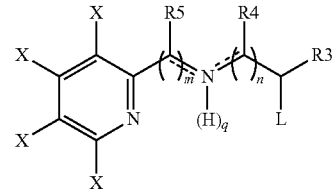

wherein

L is a phosphine (PR$^1$R$^2$);

the dotted lines simultaneously or independently represent single or double bonds, wherein when a single bond joins the carbon atom or atoms bound to R$^4$ or R$^5$ or both, R$^4$ or R$^5$ or both are additionally bound to an H;

R$^1$ and R$^2$ are each independently H, or a $C_1$-$C_{20}$ linear alkyl, a $C_3$-$C_8$ cycloalkyl, or a $C_5$-$C_{20}$ aryl, each of which is optionally substituted;

R$^3$ is H;

R$^4$ is H;

R$^5$ is H;

each X is independently H, a linear $C_3$-$C_8$ alkyl, a branched $C_3$-$C_8$ alkyl, a cyclic $C_3$-$C_8$ alkyl, a $C_3$-$C_8$ alkenyl, or a $C_5$-$C_8$ aryl, each of which is optionally substituted, or OR, F, Cl, Br, I or NR$_2$; or when taken together, two of the X groups together form an optionally substituted saturated ring, partially saturated ring, aromatic ring, or heteroaromatic ring;

R is H, a $C_1$-$C_{20}$ linear alkyl, a $C_3$-$C_{20}$ branched alkyl, a $C_3$-$C_8$ cycloalkyl, or a $C_5$-$C_8$ aryl, each of which may be optionally substituted;

each n and m is independently 1 or 2;

q is 0 or 1; and $\mu^N$ indicates that each LNN' ligand in the complex of Formula (III) includes a nitrogen atom that bridges two M atoms.

2. The complex of claim 1, wherein in the compound is:

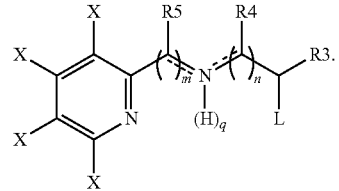

3. The complex of claim 1, wherein LNN' is

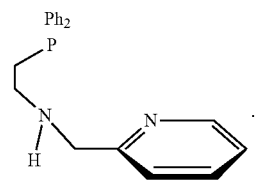

4. The complex of claim 1 which has the structure of any one of

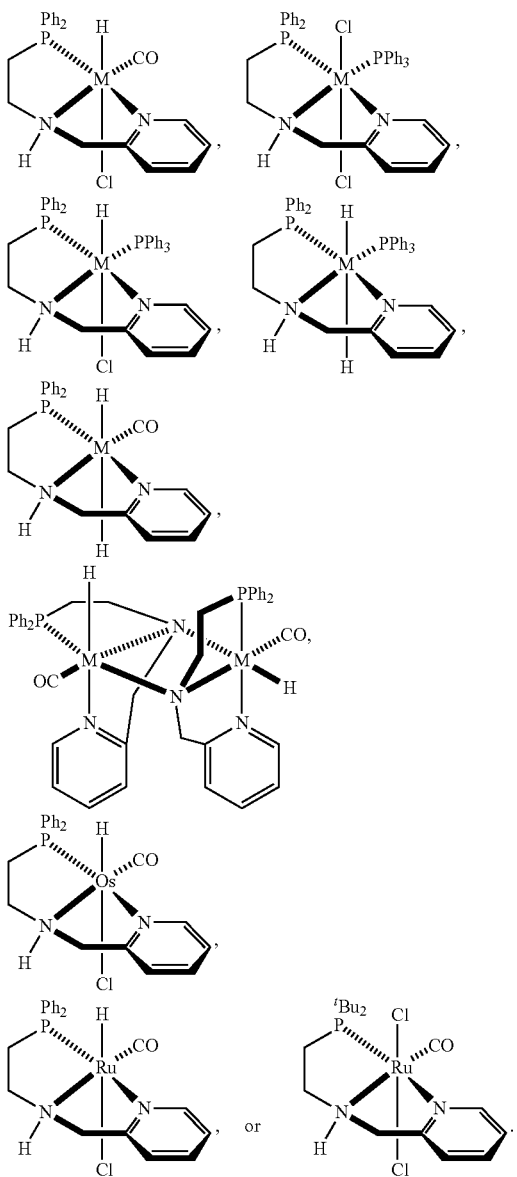

5. A process for hydrogenation of a substrate comprising treating the substrate with a catalytic amount of a complex of Formula II or III

[M(LNN')Z$_a$]   (II)

μ$^N$[M(LNN')Z$_a$]$_2$   (III)

according to claim 1 in the presence of molecular hydrogen,
wherein the hydrogenation is performed at a temperature in a range from 40° C. to 100° C. for a time in a range of 1 to 22 hours, and under 50 Bar pressure.

6. The process of claim 5, wherein the substrate comprises at least one ester; and/or
wherein the process proceeds in the presence of molecular hydrogen according to one of the following schemes

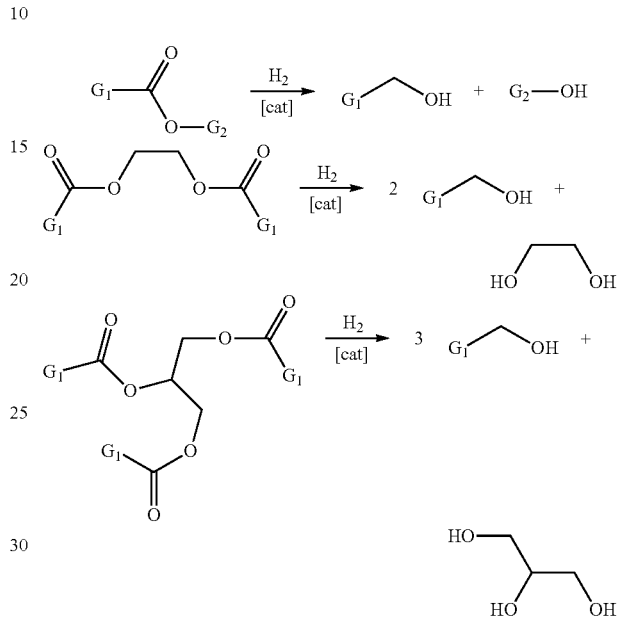

wherein G$_1$ and G$_2$, simultaneously or independently, represent a linear C$_1$-C$_{40}$ or branched or cyclic C$_3$-C$_{40}$ alkyl, alkenyl or aromatic group, any of which may be optionally substituted.

7. The process of claim 5, wherein the substrate and product pair of the hydrogenation reaction comprises:

| Hydrogenation Substrate | Product |
| --- | --- |
| ester | alcohol |
| lactone | diol. |

8. The process of claim 5, which is a solvent-free process.

9. A process for producing ethyl acetate comprising treating ethanol with a catalytic amount of a complex of Formula II or III

[M(LNN')Z$_a$]   (II)

μ$^N$[M(LNN')Z$_a$]$_2$   (III)

according to claim 1.

* * * * *